(12) United States Patent
Lawn et al.

(10) Patent No.: US 7,049,131 B1
(45) Date of Patent: May 23, 2006

(54) METHODS AND DEOXYRIBONUCLEIC ACID FOR THE PREPARATION OF TISSUE FACTOR PROTEIN

(75) Inventors: Richard M. Lawn, San Francisco, CA (US); Gordon A. Vehar, San Carlos, CA (US); Karen L. Wion, Millbrae, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 08/437,989

(22) Filed: May 10, 1995

Related U.S. Application Data

(60) Continuation of application No. 08/167,785, filed on Dec. 15, 1993, now abandoned, which is a division of application No. 07/969,863, filed on Oct. 30, 1992, now abandoned, which is a division of application No. 07/620,431, filed on Nov. 30, 1990, now abandoned, which is a continuation of application No. 07/035,409, filed on Apr. 7, 1987, now abandoned, which is a continuation-in-part of application No. 07/013,743, filed on Feb. 12, 1987, now abandoned.

(51) Int. Cl.
*C12N 15/00* (2006.01)
*C07H 21/02* (2006.01)
*C07K 14/00* (2006.01)

(52) U.S. Cl. ............... 435/320.1; 536/23.1; 435/252.3; 435/325; 530/350

(58) Field of Classification Search ............... 536/23.5, 536/23.1; 435/320.1, 240.2, 69.1, 252.3, 435/325
See application file for complete search history.

(56) References Cited

U.S. PATENT DOCUMENTS

| 4,727,028 A | * | 2/1988 | Santerre et al. ........... 435/240.2 |
| 4,959,314 A | * | 9/1990 | Mark et al. ................ 435/69.1 |
| 5,030,576 A | * | 7/1991 | Dull et al. ................. 435/69.7 |

OTHER PUBLICATIONS

Fisher et al. 1987 Thrombosis Research 48:89-99.*
Guha et al. 1986. Proc. Natl. Acad. Sci 83:299-302.*
Ullrich et al. 1984. The EMBO J. 3(2):361-364.*
Dayhoff et al. 1972. *Atlas of Protein Sequence and Structure*, 5:89-99.*
Aebersold et al. 1986. *Protides of the Biological Fluids Proceedings of the Colloquium*, 34; Brussels, Belgium, Pergamon Press, Oxford, England, pp. 715-718.*
Andoh et al. 1986. Thrombosis Research 43:275-286.*
Wilkinson, J.M. 1986. Practical Protein Chemists—A Handbook, John Wiley & Son's Ltd., pp. 121-148.*
Morrissey, J. H. et al. 1986. Abstract # 1632 of American Heart Assn. Meeting, Nov. 19, 1986.*
Day, 1983. How to Write and Publish a Scientific Paper, iSi Press; Philadelphia PA, pp. 15-19.*
Pongo, S., 1987. Methods in Enzymology 154:450-473.*

* cited by examiner

*Primary Examiner*—Karen Cochrane Carlson

(57) ABSTRACT

DNA isolates coding for tissue factor protein and methods of obtaining such DNA and producing tissue factor protein using recombinant expression systems for use in therapeutic composition for the treatment of coagulation disorders.

22 Claims, 9 Drawing Sheets

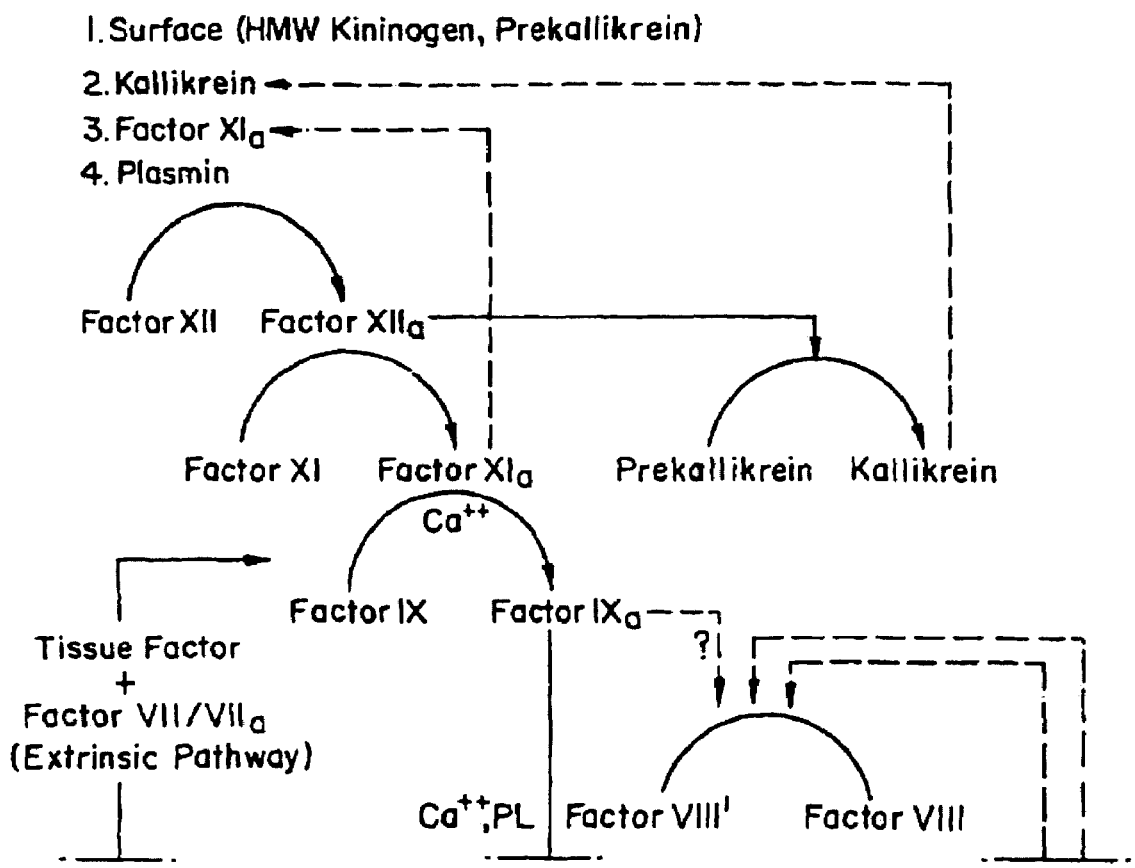

Fig. 2a.

```
1003  AGTCTACTGCAAATGCTACTATATTGCACTGTGACCGAGAACTTTTAAGAGGATAGAATACATGGAAACGCAAATGAGTATTTCGGAGCATGAAGACCCTGGAG
      TCGATGACGTTTACGATGATAATTGCACTGACACTGGCTCTTGAAAATTCTCCTATCTTTGCGTTACTACTTGAAATGGTACTACAACCAAT
1103  TTCAAAAAACTTCTGATATGACCTGTTATTACCATGGCACCTTGCACATCAGCATTGAAATGTAACGTAACGAATGGTACTACAACCAAT
      AGTTTTTTGAGAACTTATACTGGACAATAATGGTACTCGTAATCGTAGTCGTAATCAGTGTCGTAATCAGTGTAAACTTACATGATGTTGGTTA
1203  TCCAACTTTTAATTTTAACACATGGCACCTTTCTTAGATTATATATTCCGCACTCAAGGAGTAACCAGGTCTGTCCAAGCAAAAA
      AGTTCAAAATTAAAAATTGTAGTGTATTGTAACGAAATCTAATATATAAGGGCGAGTCCTCATGTGGTCCAGCAGGTCCGTTCGTTTT
1303  CAAATGGGAAATGTCTTAAAAATCTCGGTGGACTTTTGAAAAGCTTTTTTTTTTGAGACGGAGTCTGCTCTGTTGCCCAGGCTGCA
      GTTTACCCTTTTACAGAATTTTTAGGACCACCTGAAACTTTCGAAAAACTCTGCCTCAGAACGAGACAACGGTCCGACCT
1403  GTGCAGTAGCACGATCTCGGCTCACTGCACCCTCGTCTCGGGTTCAAGCAATTGTCTGCCTCAAGCCTCAGCCTCCGAGTAGCTGGATTACAGGTGCGCACT
      CACCTCATCCCAGCTAATTTTTGTATTTTTAGTAGACATGGGGTTTCACCATGTTAGCAGGCTGGTCTCGAACTCCTGACCTCAGGTGATCCACCCACCT
1503  ACCACACCAAGCTAATTTTTGTATTTTTAGTAGACATCTCTACCCCAAGTGGTAGAACCGGTCCGACCAGAACTTAAGGACTGGTCAACTAGGTGGGTGGA
      TGGTCTGGTTTCGATTAAAAACATAAATCATCCTAACGGTTCCCAAAGTCCCAAGCCCATGCCGAAAACTCCCCGACTTGGTCGGCTTTGAAATCCATGTAGGAAAACGTAAATGGAA
1603  TGGCCTTCCCAAAGTCCCAAGCCCATGCCGAAAACTCCCCGACTTGGTCGGCTTTGAAATCCATGTAGGAAAACGTAAATGGAA
      ACCGAGGGTTTCAAACCCAACTGGTACCCACTGGTCGTACGGTCGGCTTTCGAAACTCCCGACTGAAGTAGGTACATCCTTCATTTTACCTT
1703  GGAAATTGGGTGGTGCATTTCTAGGACTTTTCTAACATATGTCTATATAATAGTGTTAGGTTCTTTCTTTTTTTTCAGGAATACATTTGGAAATTCAAAACAAT
      CCTTAACCACCACGATCCTAAAGATCCTGAAAAGATTGTATACAGATTATATATCAAGAAAAAAAGTCCTTATGTAAACCTTAAGTTTTGTTA
1803  TGGCAACTTGTATTAATGTCTAAGTGCAGGAGACGATGGTATTCTGGGCAACCCGTGGAAGGATTATACGAAATGTTAGGTACTTAAGCCTTAACTCGCACTTAAGCTAAGTGGC
      ACCGTTGAAACATTCACGTCCTCAACAATTCTGAAAATATTTCGATGATATGTTTGATGTCTCAAATACTAAATTCCATGATACAACTGTAACATA
1903  ATTAAACATTTGAGAGCTAACTATATTTTATAAGACTACTATACAAACTACAGAGTTTATGATTAAGGTACTTAAGCTTCTATGGTTGACATTGTAT
      TAATTGTAAACTTCGATTGAAATATTCTGAAGAACTAAATACTAAATTGTTCGAAGATACAACTGTAACATA
2003  ATATAATTTTTTAAAAAGGTTTCTATGGGGATTTCTATTTATGTAGGTAATATATTGTTCTATTTGTATATATTGAGATAATTATTAATATACTTT
      TATATTAAAAATTTTAAAAAGATATACCCCTAAAAGATAAATACAACCCTTATATACAAGATAAACATATCCATTATAACAAGATAAACATATCCATTAT
2103  AAATAAGGTGACTGGGAATTGTTA
      TTTATTCCACTGACCCTTAACAAT
```

```
                                              hinPI
                                              hhaI
                                              nlaIV
                                sau96I         narI
                                mspI           haeII
                                hpaII          banI
                  nael          scrFI                     mnlI    bglI    ahaII          nlaIV                         sau3AI                      accI nlaIII
         mnlI   eaeI haeII      bstNI     ahaII           acctcccag cccacgggc gccacggaac           cggtcgatc tcgccggcca agtctacact ctggtagaca
  1   ctcggcactcc cctggccgcg cccaggggcg cttcagccca   tggagggtc gggtgccgg cggtgccttg                gccgagtag agcggcccgt gaccatctgt
      gagccgtgagg ggaccggcgc gggtccccgc gaagtcgggt scrFI
                                ncII
                                mspI
                                hpaII                                                                              hinPI
                                smaI sau96I                                                                        hhaI
                                scrFI                                                                              nlaIV
                     sau96I ppuMI                                                                                  narI
                      nlaIV nlaIV                                                                                  haeII
                     haeIII ecoO thaI                                                                              banI
                     scrFI ncII nlaIV hinPI                                      hgaI                             scrFI    hhaI
                     bstNI avaI avaII hhaI avaI          cggccctccgc tgctcggctg             cggacgctcc            bglI    haeIII mspI
                     fnu4HI                              gcgggaggcg acgagccgac             gcctgcgagg             mboII bstNI chaI haeII cggcttcagg
                                                                                                                 caggtggccg cggcttcagg
  101 tggagacccc tgcctggccc cggtccgcg                                                                           gcccaagtccccac cccgccgaa
      acctctgggg acggaccggg gccaggggcc mspI
                                                                                           nlaIV                            hpaII
                                                                                                                            naeI haeII
                                                                         scrFI                                              scrFI                    acII
                                                      hgaI               bstNI      mboII bstNI caeI haeII                                           agtctacact
                  fnu4HI
  201 cactacaaat actgtggcag catatataatt aacttggaaa tcaagacaat tttggagtgg gaaccgaccc cgtcaatca agtctacact
      gtgatgttta tgacaccgtc gtatattaa ttgaacctt agttgctta aaaccctcacc cttgggtcgg gcagtagt tcagatgtga hphI
                                                                                                   draIII           mnII                   foxI
  301 gttcaaataa gcactaagtc aggagkttgg aaaagcaaat gctttttacac aacagacaca gagtgtgacc tcaccgacga gattgtgaag gatgtgaagc
      caagttatt cgtgattcag tcctctaacc tttttcgttta cgaaaatgtg ttgtctgtgt ctcacactgg ctaacactgct ctacacttcg mspI
                                       hpaII
                                       scrFI
                                       ncII                         mspI hpaII                     nlaIV
                                 mboII                     hgiAI    bsp1286
  401 agagtactt ggcacgggtc ttctcctacc cggcagggaa tgtgagagc accggttctg ctgggaggcc accccctcgg ctgaggggtc aacttcccag acttccacacc
      tctgcatgaa cccgtgccag aagaggatgg gccgtccctt acactctcg tggccaagtc tggccctctct tgtgccagac gaccccctcg agacataccc ttgaggggtc tcaagtgtgg mnlI                                                                                          mboII
      rsaI
  501 ttaccggag acaaacctcg gacagccaac aattcagagt tgggaacaaa acggtagagag acgtgaatgtc accgtagaag tttagtcaga
      aatggaccctc tgtttggagc ctgtcggttg ttaagtctca accctcgttt tcaacttgtcc tgcatctcc tactgcctg aatcagtct
```

Fig.3b.

```
                        scrFI
                        ncII
                        mspI
                        hpaII
              ddeI      mnlI  fokI                                              mboII                           mspI
                                                                                                                hpaII   mboII
                                                                                                        hpaI    hincII  rsaI
601 AGGAACAACA CTTTCCTAAG CCTCCCGGAT GTTTTGGCA AGGACTTAAT TATATACACTT TATTATTGGA AATCTTCAAC TTCAGGAAAG AAAACACCCA
    TCCTTGTTGT GAAAGGATTC GGAGGGCCTA CAAAACCGT TCCTGAATTA ATATATGTGAA ATAATAACCT TTAGAAGTTG AAGTCCTTTC TTTTGTCGGT mspI                                                                  hinfI           mnlI
              hpaII                                                                 mnlI           mboII
              scrFI                                            scrFI                hpaII         mboII
              ncII                                             bstNI
701 AAACAAACAC TAATGAGTTT TTGATTGATG AGAAAACTAC TGTTTCAGTG TTCAAGCAGT GATTCCCTCC CGAACAGTTA ACCGGAAGAG
    TTTGTTTGTG ATTACTCAAA AACTAACTAC TCTTTTGATG ACAAAGTCAC AAGTCGTCA ACTAAGGGAGG GCTTGTCAAT TGGCCTTCTC scrFI
                        bstNI                                                                               fokI
                        haeIII                ecoRI         sspI                    alutI
                        sau96I                                                                              fokI
801 TACAGACAGC CCGGTAGAGT GTATGGGCCA GGAGAAAGGA CCCCTTTCCC GAATTCACAG AAATATCTA CATCATTGGA GCTGTGGTAT TTGTGGTCAT CATCCTTCTC
    ATGTCTGTCG GGCCATCTCA CATACCCGGT CCTCTTTCCT GGGGAAAGGG CTTAAGTCTC TTTATAGAT GTAGTAACCT CGACACCATA AACACCAGTA GTAGGAACAG scrFI
    bstNI                                                  alutI
                                                                                                                            mboII  scrFI
    fokI                                                                          alaIII                                    nlaIII bstNI
901 ATCATCCTGG CTATATCCCT ACACAAGTGT AGAAGGCAAG GAGTGGGGCA GACCTGGAAG CTCGACCTTC GAGAACTCCC CACTGAATGT TTCATAAAGG AAGCACTGTT
    TAGTAGGACC GATATAGGGA TGTGTTCACA TCTTCCGTTC CTCACCCCGT CTGGACCTTC GAGCTGGAAG CTCTTGAGGG GTGACTTACA AAGTATTTCC TTCGTGACAA alutI                                                          mnlI
1001 GGAGTACTG CAAATGCTAT AATGCACTGT GACCGAGAAC TTTTAAGACA ATAGAATACA TGGAAACCGA AATGAGTATT TCGGACCATG AACCAGTTCG AACCCCTGG
     CCTCGATGAC GTTTACGATA TTACGTGACA CTGGCTCTTG AAAATTCTGT TATCTTATGT ACCTTTGGCT TTACTCATAA AGCCTGGTAC TTCTGGGACC bseI
1101 AGTCCAAAA ACTCTGATA TGACCTGTTA TTACCATTAG CATTCGGGTT TTGACATGAG CATTAGTCAG TTTGAATGT AACGAATGGT ACTACACCA
     TCAAGTTTT TGAGAACTAT ACTGGACAAT AATGGTAATC GTAAGCCCAA AACTGTACTC GTAATCAGTC AAACTTACA TTGCTTACCA TGATGTTGGT nlaIV
                                           banI
                                           nlaIII           alutI
                                           styI             hindIII                                        scrFI
                                           ncoI                                                            bstNI
1201 ATTCCAAGTT TTAATTTTTA ACACCATGGC ACCTTTTGCA CATAACATGC TTTAGATTAT ATATTCCGCA CTCAAGGAGT AACCAGGTCG TCCAAGCAAA
     TAAGGTTCAA AATTAAAAAT TGTGGTACCG TGGAAAACGT GTATTGTACG AAATCTAATA TATAAGGCGT GAGTTCCTCA TTGGTCCAGC AGGTTCGTTT scrFI                                                                     hinfI             scrFI
                      bstNI                                      alutI                          tthIIII           bstNI
1301 AACAAATGGG AAAAATCCT GGTGGACTG AAAAAAGCT TTGAAAAGCT TTGGAAAGCT AACTTTTCGA TTTTTTTTTT AAAAAAAAAA AGACGGAGTC TTGCTCTGTT GCCCAGGCTG
     TTGTTTACCC TTTTTAGGA CCACCTGAAC TTTTTTTCGA AACTTTTCGA TTGAAAAGCT TGAAACCT AAAAAAAAAA TTTTTTTTTT TCTGCCTCAG AACGAGACAA CGGGTCCGAC ddeI
                                      mnlI                                                                 hinPI
                      sauJAI           mnlI    aval         alutI                                          hhaI
                      dphI                                                                                 mstI
                                                                                                           fspI
1401 GAGTCCAGTA GCACGATCTC GGCTCACTGC ACCCGGGTC TCTCGGGTTC AAGCAATTGT CTCCCGAGTA GTGGGATTA CAGGCGCGCA TCCAAGGCGT
     CTCAGGTCAT CGTGCTAGAG CCGAGTGACG TGGGGCCCAG AGAGCCCAAG TTCGTTAACA GAGGGCTCAT CACCCTAAT GTCCGCGCGT
```

```
                          scrFI
                          bstNI
                          haeIII
                          haeI                                          ddeI  sau3AI
              aluI        eaeI                             hphI         mnlI  dpnI    styI
     CTACCACACC AAGCTAATTT TTGTATTTT TAGTAGAGAT GGGTTCAC CATCTTGGCC AGGCTGGTCT TGAATTCCTG ACCTCAGTTG ATCCACCCAC
1501 GATGGTGTGG TTCGATTAAA AACATAAAAA ATCATCTCTA CCCAAAGTG GTAGAACCGG TCCGACCAGA ACTTAAGGAC TGGAGTCAAC TAGGTGGGTG
     mnlI
     haeIII
     haeI                                         nlaIII                               nlaIII
     CTTGGCCTCC CAAAGTGCTA CGTGAACCAC CATGCCCAGC TTGAGGGGCT GACTTCAATC CATGTAGGAA AGTAAATGG
1601 GAACCGGAGG GTTTCACGAT GCACTTGGTG GTACGGGTCG AACTCCCGA CTGAAGTTAG GTACATCCTT TCATTTACC
                                       aluI
                              ddeI     hindIII  mnlI
     AAGGAATTG GGTGCATTTC TAGGACTTTT CATATATAT AGTGTTAGG TTCTTTTTT ACATTTGGAA ATTCAAACA
1701 TTCCTTAAC CCACGTAAAG ATCCTGAAAA AGATATATA TCACAATCC AAGAAAAAA TGTAAACCTT TAAGTTTGT
                                       nlaIV
                                       banI
     ATTGGCAAAC TTTGTATTAA TGTGTTAAGT GGGCACCTTC CTAATATGCT TTACAATCTG CACTTTAACT GACTTAAGTG
1801 TAACCGTTTG AAACATAATT ACACAATTCA CCCGTGGAAG GATTATACGA AATGTTAGAC GTGAAATTGA CTGAATTCAC
              aluI                                                           aluI
              ahaIII                                          rsaI           hindIII       hincII
     GCATTAAACA TTTGAGAGCT AACTATATTT ACTATACAAA CTACAGAGTT TATGATTAA GGTACATTAA GCTTCTATGG TTGACATTCT
1901 CGTAATTTGT AAACTCTCGA TTGATATAAA TGATATGTTT GATGTCTCAA ATACTAAATT CCATGAATT CGAAGATACC AACTGTAACA
     draI                                                                                    draI
     ahaIII                                                                                  ahaIII
     ATATATAATT TTTTAAAAAG GTTTTCTATA TGGGGATTTT CTTTCTATTG AGGTAATATT GTTCTATTTG GATAATTTAT TTAATATACT
2001 TATATATTAA AAAATTTTTC CAAAAGATAT ACCCCTAAAA GAAAGATAAC TCCATTATAA CAAGATAAAC CTATTAAATA AATTATATGA
     hphI
     TTAAATAAAG GTGACTGGGA ATTGTTA
2101 AATTTATTTC CACTGACCCT TAACAAT Fig.3c
```

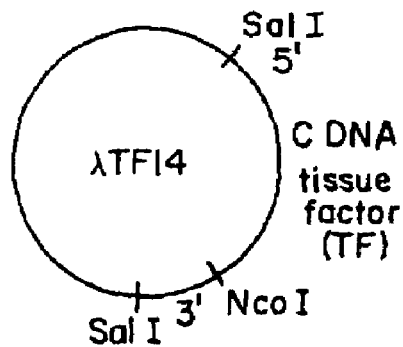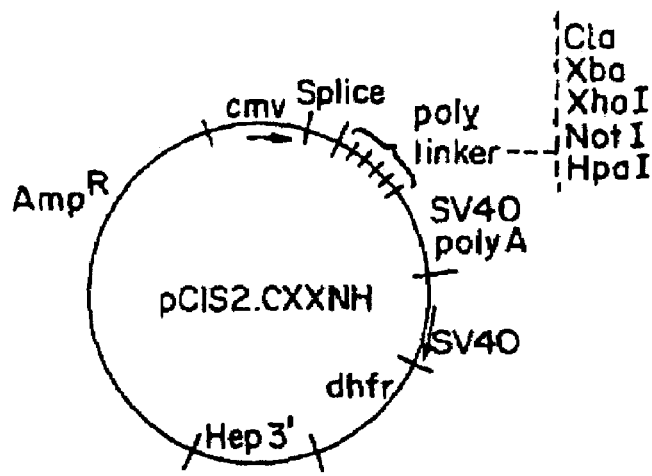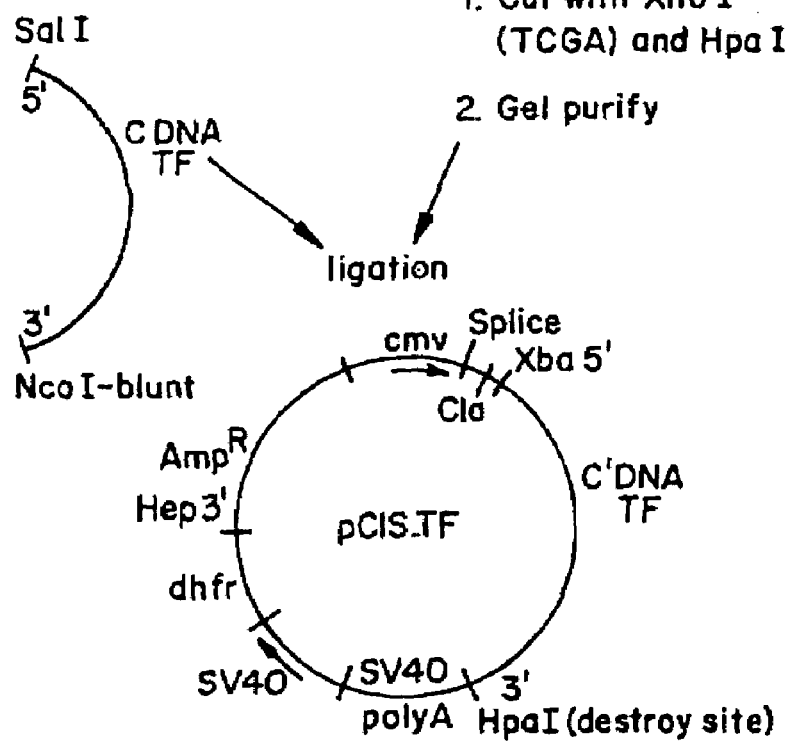
Fig. 4.

METHODS AND DEOXYRIBONUCLEIC ACID FOR THE PREPARATION OF TISSUE FACTOR PROTEIN

This application is a continuation of U.S. Ser. No. 08/167,785, filed Dec. 15, 1993, now abandoned, which is a divisional of U.S. Ser. No. 07/969,863 filed Oct. 30, 1992, now abandoned, which is a divisional of U.S. Ser. No. 07/620,431, filed Nov. 30, 1990, now abandoned, which is a continuation of U.S. Ser. No. 07/035,409, filed Apr. 7, 1987, now abandoned, which is a continuation-in-part of U.S. Ser. No. 07/013,743, filed Feb. 12, 1987, now abandoned.

BACKGROUND

This invention relates to tissue factor protein. The invention further relates to novel forms and compositions thereof, and particularly to the means and methods for production of tissue factor protein to homogeneity in therapeutically significant quantities. This invention also relates to preparation of isolated deoxyribonucleic acid (DNA) coding for the production of tissue factor protein, to methods of obtaining DNA molecules which code for tissue factor protein, to the expression of human tissue factor protein utilizing such DNA, as well as to novel compounds, including novel nucleic acids encoding tissue factor protein or fragments thereof. This invention is also directed to tissue factor protein derivatives, particularly derivatives lacking the near C-terminal hydrophobic portion of the protein, and their production by recombinant DNA techniques.

Bleeding is one of the most serious and significant manifestations of disease. It may occur from a local site or may be generalized. Primary hemostasis consists principally of two components: vasoconstriction and platelet plug formation. Platelet plug formation may be divided into several stages: adhesion of platelets to subendothelial surfaces exposed by trauma; platelet activation release reaction; platelet aggregation, which results in the sequestration of additional platelets at the site, and the binding of fibrinogen and the coagulation proteins to the platelet surface which results in thrombin formation; and, fusion which is the coalescence of fibrin and fused platelets to form a stable haemostatic plug.

Blood coagulation performs two functions; the production of thrombin which induces platelet aggregation and the formation of fibrin which renders the platelet plug stable. A number of discrete proenzymes and procofactors, referred to as "coagulation factors", participate in the coagulation process. The process consists of several stages and ends with fibrin formation. Fibrinogen is converted to fibrin by the action of thrombin. Thrombin is formed by the proteolytic cleavage of a proenzyme, prothrombin. This proteolysis is effected by activated factor X (referred to as factor $X_a$) which binds to the surface of activated platelets and, in the presence of factor Va and ionic calcium, cleaves prothrombin.

Activation of factor X may occur by either of two separate pathways, the extrinsic or the intrinsic (FIG. 1). The intrinsic cascade consists of a series of reactions wherein a protein precursor is cleaved to form an active protease. At each step, the newly formed protease will catalyze the activation of the precursor protease at the subsequent step of the cascade. A deficiency of any of the proteins in the pathway blocks the activation process at that step, thereby preventing clot formation and typically gives rise to a tendency to hemorrhage. Deficiencies of factor VIII or factor IX, for example, cause the severe bleeding syndromes haemophilia A and B, respectively. In the extrinsic pathway of blood coagulation, tissue factor, also referred to as tissue thromboplastin, is released from damaged cells and activates factor X in the presence of factor VII and calcium. Although activation of factor X was originally believed to be the only reaction catalyzed by tissue factor and factor VII, it is now known that an amplification loop exists between factor X, factor VII, and factor IX (Osterud, B. and S. I. Rapaport, Proc. Natl. Acad. Sci. [USA] 74:5260–5264 [1977]; Zur, M. et al., Blood 52: 198 [1978]). Each of the serine proteases in this scheme is capable of converting by proteolysis the other two into the activated form, thereby amplifying the signal at this stage in the coagulation process (FIG. 1). It is now believed that the extrinsic pathway may in fact be the major physiological pathway of normal blood coagulation (Haemostasis 13:150–155 [1983]). Since tissue factor is not normally found in the blood, the system does not continuously clot; the trigger for coagulation would therefore be the release of tissue factor from damaged tissue.

Tissue factor is an integral membrane glycoprotein which, as discussed above, can trigger blood coagulation via the extrinsic pathway (Bach, R. et al., J. Biol. Chem. 256[16]: 8324–8331 [1981]). Tissue factor consists of a protein component (previously referred to as tissue factor apoprotein-III) and a phospholipid. Osterud, B. and Rapaport, S. I., Proc. Natl. Acad. Sci. 74, 5260–5264 (1977). The complex has been found on the membranes of monocytes and different cells of the blood vessel wall (Osterud, B., Scand. J. Haematol. 32: 337–345 [1984]). Tissue factor from various organs and species has been reported to have a relative molecular mass of 42,000 to 53,000. Human tissue thromboplastin has been described as consisting of a tissue factor protein inserted into a phospholipid bilayer in an optimal ratio of tissue factor protein:phospholipid of approximately 1:80 (Lyberg, T. and Prydz, H., Nouv. Rev. Fr. Hematol. 25(5): 291–293 [1983]). Purification of tissue factor has been reported from various tissues such as,: human brain (Guha, A. et al. Proc. Natl. Acad. Sci. 83: 299–302 [1986] and Broze, C. H. et al., J. Biol. Chem. 260[20]: 10917–10920 [1985]); bovine brain (Bach, R. et al., J. Biol. Chem. 256: 8324–8331 [1981]); human placenta (Bom, V. J. J. et al., Thrombosis Res. 42:635–643 [1986]; and, Andoh, K. et al., Thrombosis Res. 43:275–286 [1986]); ovine brain (Carlsen, E. et al., Thromb. Haemostas. 48[3], 315–319 [1982]); and, lung (Glas, P. and Astrup, T., Am. J. Physiol. 219, 1140–1146 [1970]). It has been shown that bovine and human tissue thromboplastin are identical in size and function (see Broze, G. H. et al., J. Biol. Chem. 260[20], 10917–10920 [1985]). It is widely accepted that while there are differences in structure of tissue factor protein between species there are no functional differences as measured by in vitro coagulation assays (Guha et al. supra). Furthermore, tissue factor isolated from various tissues of an animal, e.g. dog brain, lung, arteries and vein was similar in certain respects such as, extinction coefficient, content of nitrogen and phosphorous and optimum phospholipid to lipid ratio but differed slightly in molecular size, amino acid content, reactivity with antibody and plasma half life (Gonmori, H. and Takeda, Y., J. Physiol. 229[3], 618–626 [1975]). All of the tissue factors from the various dog organs showed clotting activity in the presence of lipid. Id. It is widely accepted that in order to demonstrate biological activity, tissue factor must be associated with phospholipids in vitro (Pitlick, F. A., and Nemerson, Y., Biochemistry 9: 5105–5111 [1970] and Bach, R. et al. supra. at 8324). It has been shown that the removal of the phospholipid component of tissue factor, for example by use of a phospholipase, results in a loss of its biological activity in vitro (Nemerson, Y., J. C. I. 47: 72–80 [1968]). Relipidation can restore in vitro tissue factor activity (Pitlick. F. A. and Nemerson, Y., supra and Freyssinet, J. M. et al., Thrombosis and Haemostasis 55: 112–118 [1986]). An amino terminal sequence of tissue factor (Bach, R. et al., Am. Heart Assoc. [November, 1986], Morrissey, J. H. et al., Am. Heart Assoc. [November, 1986]) and a CNBr peptide fragment (Bach, R. et al. supra) have been determined.

Infusion of tissue factor has long been believed to compromise normal haemostasis. In 1834 the French physiologist de Blainville first established that tissue factor contributed directly to blood coagulation (de Blainville, H. Gazette Medicale Paris, Series 2, 524 [1834]). de Blainville also observed that intravenous infusion of a brain tissue suspension caused immediate death which he observed was correlated with a hypercoagulative state giving rise to extensively disseminated blood clots found on autopsy. It is now well accepted that intravenous infusion of tissue thromboplastin induces intravascular coagulation and may cause death in various animals (Dogs: Lewis, J. and Szeto I. F., J. Lab. Clin. Med. 60: 261–273 [1962]; rabbits: Fedder, G. et al., Thromb. Diath. Haemorrh. 27: 365–376 [1972]; rats: Giercksky, K. E. et al., Scand. J. Haematol. 17: 305–311 [1976]; and, sheep: Carlsen, E. et al., Thromb. Haemostas. 48: 315–319 [1982]).

Although the isolation of tissue factor has been described in the literature as shown above, the precise structure of tissue factor protein has not been previously established. While some quantities of "purified" tissue factor protein have been available as obtained from various tissues, the low concentration of tissue factor protein in blood and tissues and the high cost, both economic and of effort, of purifying the protein from tissues makes this a scarce material. It is an object of the present invention to isolate DNA encoding tissue factor protein and to produce useful quantities of human tissue factor protein using recombinant techniques. It is a further object to prepare novel forms of tissue factor protein. This and other objects of this invention will be apparent from the specification as a whole.

SUMMARY OF THE INVENTION

Objects of this invention can be accomplished by a method, comprising: identifying and cloning the cDNA which codes for human tissue factor protein; incorporating that cDNA into a recombinant DNA vector; transforming a suitable host with the vector including that DNA; expressing the human tissue factor protein DNA in such a host; and recovering the human tissue factor protein that is produced. Similarly, the present invention makes it possible to produce human tissue factor protein and/or derivatives thereof by recombinant techniques, as well as to provide products and methods related to such human tissue factor protein production. The isolation and identification and sequencing of the tissue factor protein DNA was difficult. The mRNA was rare and no other source of large quantities of mRNA was known, and heretofore no complete amino acid sequence for tissue factor protein was known.

The present invention is directed to the compositions and methods of producing human tissue factor protein via recombinant DNA technology, including: 1) the isolation and identification of the entire DNA sequence of the protein and the 5' and 3'-flanking region thereof; 2) the construction of cloning and expression vehicles comprising said DNA sequence, enabling the expression of the human tissue factor protein, as well as methionine, fusion or signal N-terminus conjugates thereof; and 3) viable cell cultures, genetically altered by virtue of their containing such vehicles and capable of producing human tissue factor protein. This invention is further directed to DNA compositions and methods of producing DNA which codes for cellular production of human tissue factor protein. Yet another aspect of this invention are new compounds, including DNA sequences which are utilized in obtaining clones which encode tissue factor protein. Still another aspect of the present invention is tissue factor protein essentially free of all naturally occurring substances with which it is typically found in blood and/or tissues, i.e., the tissue factor protein produced by recombinant means will be free of those contaminants with which it is typically associated when isolated from its in vivo physiological milieu. One noteworthy potential contaminant is the causative agent for acquired immune deficiency syndrome (AIDS), which is being found in the circulation of ever increasing numbers of individuals. Depending upon the method of production, the tissue factor protein hereof may contain associated glycosylation to a greater or lesser extent compared with material obtained from its in vivo physiological milieu, i.e. blood and/or tissue. This invention is further directed to novel tissue factor protein derivatives, in particular derivatives lacking the signal sequence and the hydrophobic portion of the protein near the C-terminal end of the protein comprising the amino acid sequence which constitutes the tissue factor protein transmembrane or membrane binding domain.

The utility of the human tissue factor protein and derivatives thereof of this invention is based in part on the novel and unexpected observation that infusion into hemophilia dogs of tissue factor protein, that is the protein portion of tissue factor lacking the naturally occurring phospholipid, which was previously referred to as tissue factor apoprotein III and previously believed to be inactive, corrected the haemostatic deficiency. Tissue factor protein was for the first time found to correct the bleeding diathesis, i.e. a tendency toward hemorrhage, associated with factor VIII deficiency in vivo. Infusion of tissue factor protein would be expected to be ineffective in light of the prior art papers which describe tissue factor as having an absolute requirement for phospholipid. In contrast to the work of de Blainville and subsequent researchers over the next one hundred and fifty-two (152) years, tissue factor protein was also found to be nontoxic to the dogs when infused intravenously.

The human tissue factor protein and derivatives thereof of this invention are useful in the treatment of various chronic bleeding disorders, characterized by a tendency toward hemorrhage, both inherited and acquired. Examples of such chronic bleeding disorders are deficiencies of factors VIII, IX, or XI. Examples of acquired disorders include: acquired inhibitors to blood coagulation factors e.g. factor VIII, von Willebrand factor, factors IX, V, XI, XII and XIII; haemostatic disorder as a consequence of liver disease which includes decreased synthesis of coagulation factors and DIC; bleeding tendency associated with acute and chronic renal disease which includes coagulation factor deficiencies and DIC; haemostasis after trauma or surgery; patients with disseminated malignancy which manifests in DIC with increases in factors VIII, von Willebrand factor and fibrinogen; and haemostasis during cardiopulmonary surgery and massive blood transfusion. The human tissue factor protein and derivatives thereof of this invention may also be used to induce coagulation for acute bleeding problems in normal patients and in those with chronic bleeding disorders. Other uses for tissue factor protein will be apparent to those skilled in the art.

BRIEF DESCRIPTION OF THE DRAWINGS

FIG. 1 FIG. 1(I) and FIG. 1(II) are collectively referred to herein as FIG. 1. Diagram showing activation of blood coagulation via intrinsic pathway.

FIG. 2 FIGS. 2(a) and 2(b) are collectively referred to herein as FIG. 2. Nucleotide and amino acid sequence of human tissue factor protein. The nucleotide sequence of the human tissue factor protein was determined from DNA sequence analysis of one adipose clone and in part confirmed by sequencing other clones. Predicted amino acids of the tissue factor protein are shown below the DNA sequence and are numbered from the first residue of the N-terminal of the protein sequence. Negative amino acid numbers refer to the presumed leader signal sequence or preprotein, while positive numbers refer to the mature protein.

FIGS. 3a, 3b, and 3c are collectively referred to herein as FIG. 3. The human tissue factor protein cDNA and restriction enzyme sites.

FIG. 4 A contemplated procedure for the construction of expression vectors for full length tissue factor protein.

DETAILED DESCRIPTION

Figure 1:
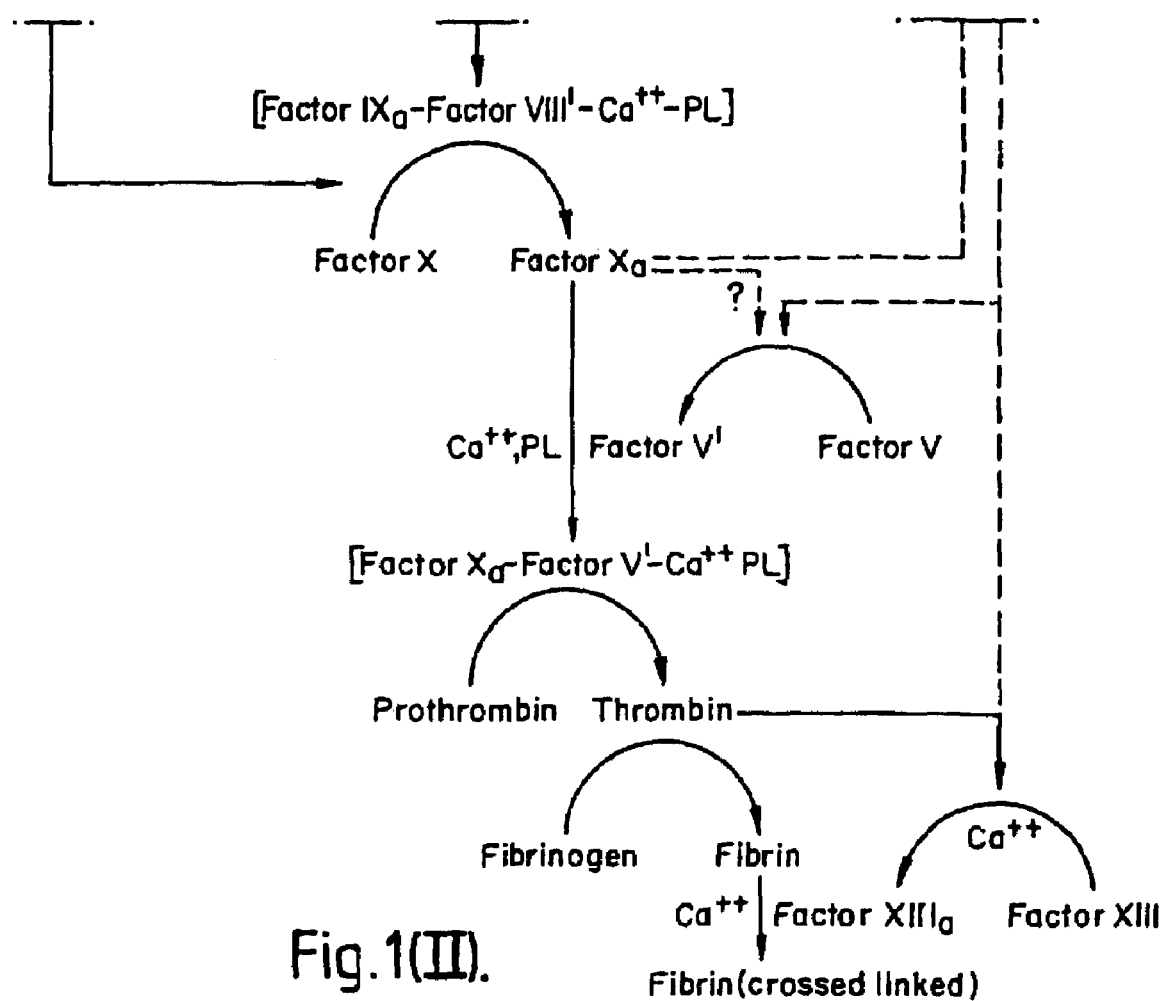

As used herein, "tissue factor protein" refers to a protein capable of correcting various bleeding disorders e.g. by inducing coagulation, particularly those disorders associated with deficiencies in coagulation factors. Tissue factor protein is distinct from tissue factor or tissue thromboplastin of the prior art in that it lacks the naturally occurring lipid portion of the molecule. Tissue factor protein also includes tissue factor protein associated with phospholipid which lipid is distinct from the naturally occurring lipid associated with tissue thromboplastin and displays coagulation-inducing capability without the concomitant toxicity observed with the lipidated protein. Infusion of tissue factor protein, as defined herein, does not result in disseminated intravascular coagulation. The capacity of tissue factor protein to correct various bleeding disorders is readily determined using various in vivo bleeding models e.g. initiation of coagulation in hemophilic dogs using cuticle bleeding time (CBT) determination (Giles, A. R. et al., Blood 60:727–730 [1982]).

Figure 2A:
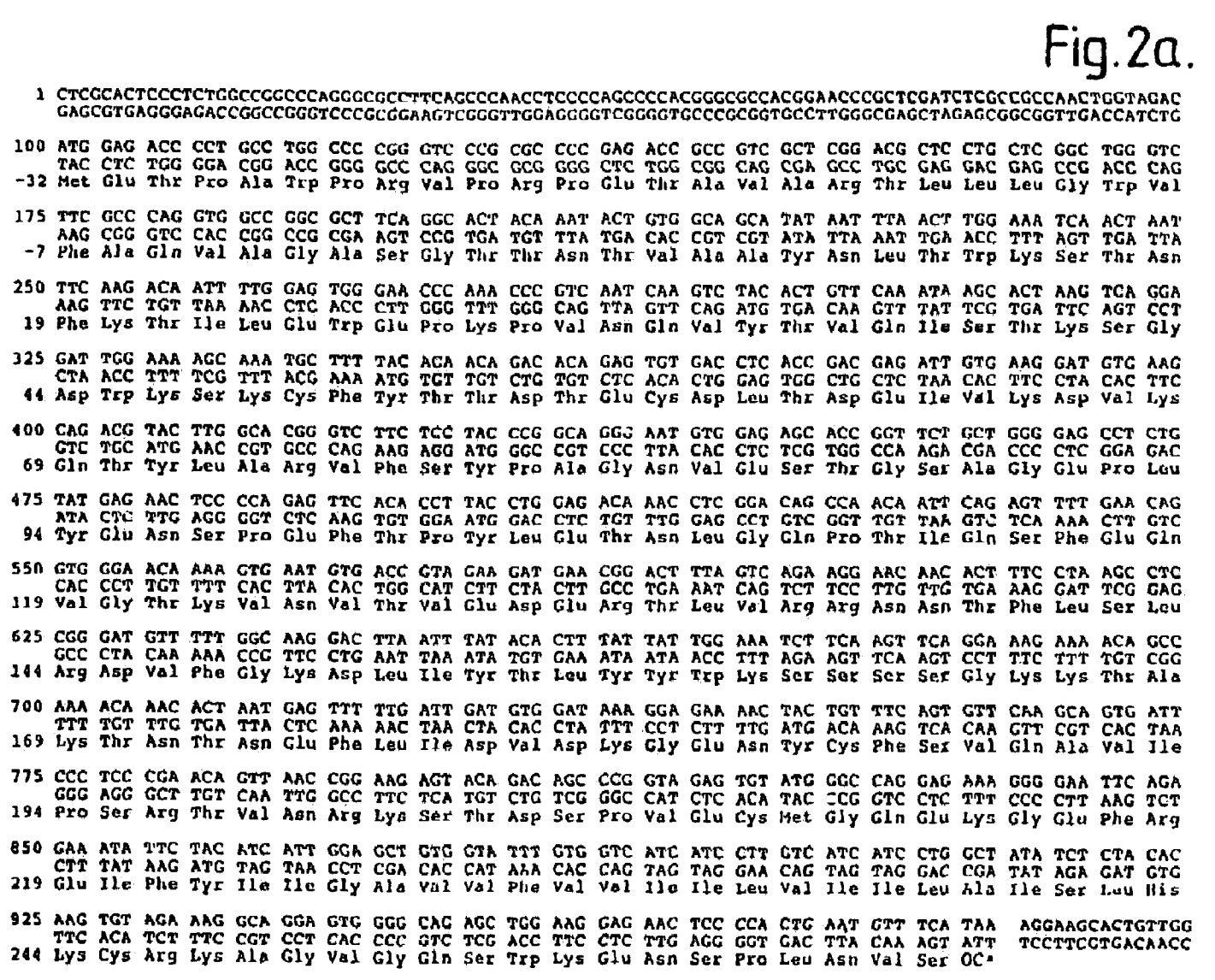

The amino acid sequence of FIG. 2 is that of pretissue factor protein. Pretissue factor protein can be expressed, for example, in prokaryotes, which do not process and secrete mature protein, by transforming with an expression vector comprising DNA encoding pretissue factor protein. It is preferable to transform host cells capable of accomplishing such processing so as to obtain mature tissue factor protein in the culture medium or periplasm of the host cell. Typically, higher eukaryotic host cells such as mammalian cells are capable of processing pretissue factor protein and secreting mature tissue factor protein upon transformation with DNA encoding pretissue factor protein.

Alternatively, secreted mature tissue factor protein can be obtained by ligating the 5' end of the DNA encoding mature tissue factor protein to the 3' end of DNA encoding a signal sequence recognized by the host cell. An expression vector comprising the ligated DNA sequences is used to transform host cells. The host cell will process the expressed fusion by proteolytically cleaving the peptide bond between the signal sequence and the first amino acid of tissue factor protein and secreting the mature tissue factor protein into the host cell periplasm or into the medium, depending upon the host cell in question. For example, in constructing a prokaryotic expression vector the human tissue factor protein secretory leader, i.e. amino acids −32 to −1, is replaced by the bacterial alkaline phosphatase or heat stable enterotoxin II leaders, and for yeast the tissue factor protein leader is replaced by the yeast invertase, alpha factor or acid phosphatase leaders. Gram negative organisms transformed with a homologous signal-tissue factor protein fusion will secrete mature tissue factor protein into the cell periplasm, whereas yeast or *bacillus* sp. will secrete mature tissue factor protein into the culture medium.

Included within the scope of the present invention are tissue factor protein having native glycosylation and the amino acid sequence as set forth in FIG. 2, analogous tissue factor proteins from other animal species such as bovine, porcine, ovine and the like, deglycosylated or unglycosylated derivatives of such tissue factor proteins, and biologically active amino acid sequence variants of tissue factor protein, including alleles, and in vitro-generated covalent derivatives of tissue factor proteins that demonstrate tissue factor protein activity.

Amino acid sequence variants of tissue factor protein fall into one or more of three classes: substitutional, insertional or deletional variants. Insertions include amino and/or carboxyl terminal fusions as well as intrasequence insertions of single or multiple amino acid residues. Fusions include hybrids of mature tissue factor protein with polypeptides that are homologous with tissue factor protein, for example, in the case of human tissue factor protein, secretory leaders from other secreted human proteins. Fusions also include hybrids of tissue factor protein with polypeptides homologous to the host cell but not to tissue factor protein, as well as, polypeptides heterologous to both the host cell and the tissue factor protein. Preferred fusions within the scope of this invention are amino terminal fusions with either prokaryotic peptides or signal peptides of prokaryotic, yeast, viral or host cell signal sequences. It is not essential that the signal sequence be devoid of any residual mature sequence from the protein whose secretion it ordinarily directs but this is preferable in order to avoid the secretion of a tissue factor protein fusion.

Insertions can also be introduced within the mature coding sequence of tissue factor protein. These, however, ordinarily will be smaller insertions than those of amino or carboxyl terminal fusions, on the order of 1 to 4 residues. A representative example is [$Arg_{135}Arg_{136} \rightarrow Arg_{135}ProArg_{137}$] tissue factor protein, a variant selected for its resistance to trypsin hydrolysis at the $Arg_{135}$ residue. Unless otherwise stated, the specific tissue factor protein variations described herein are variations in the mature tissue factor protein sequence; they are not pretissue factor protein variants.

Insertional amino acid sequence variants of tissue factor proteins are those in which one or more amino acid residues are introduced into a predetermined site in the target tissue factor protein. Most commonly, insertional variants are fusions of heterologous proteins or polypeptides to the amino or carboxyl terminus of tissue factor protein. Immunogenic tissue factor protein derivatives are made by fusing a polypeptide sufficiently large to confer immunogenicity to the target sequence by cross-linking in vitro or by recombinant cell culture transformed with DNA encoding the fusion. Such immunogenic polypeptides can be bacterial polypeptides such as trpLE, beta-galactosidase and the like.

Deletions are characterized by the removal of one or more amino acid residues from the tissue factor protein sequence. Typically, no more than about from 2 to 6 residues are deleted at any one site within the tissue factor protein molecule, although deletion of residues −31 to −1 inclusive will be undertaken to obtain met-tissue factor protein, a variant adapted for intracellular direct expression of met-mature tissue factor protein. Another deletion is of the transmembrane domain located at about residues 220 to 242 of the tissue factor protein molecule.

These variants ordinarily are prepared by site specific mutagenesis of nucleotides in the DNA encoding the tissue factor protein, thereby producing DNA encoding the variant, and thereafter expressing the DNA in recombinant cell culture. However, variant tissue factor protein fragments having up to about 100–150 residues may be conveniently prepared by in vitro synthesis. The variants typically exhibit the same qualitative biological activity as the naturally-occurring analogue, although variants also are selected in order to modify the characteristics of tissue factor protein as will be more fully described below.

While the site for introducing an amino acid sequence variation is predetermined, the mutation per se need not be predetermined. For example, in order to optimize the performance of a mutation at a given site, random mutagenesis may be conducted at the target codon or region and the expressed tissue factor protein variants screened for the optimal combination of desired activity. Techniques for making substitution mutations at predetermined sites in DNA having a known sequence are well known, for example M13 primer mutagenesis.

Amino acid substitutions are typically of single residues; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. Obviously, the mutations that will be made in the DNA encoding the variant tissue factor protein must not place the sequence out of reading frame and preferably will not create complementary regions that could produce secondary mRNA structure (EP 75,444A).

Substitutional variants are those in which at least one residue in the FIG. 2 sequence has been removed and a different residue inserted in its place. Such substitutions generally are made in accordance with the following Table 1 when it is desired to finely modulate the characteristics of tissue factor protein.

TABLE 1

| Original Residue | Exemplary Substitutions |
|---|---|
| Ala | ser |
| Arg | lys |
| Asn | gln; his |
| Asp | glu |
| Cys | ser |
| Gln | asn |
| Glu | asp |
| Gly | pro |
| His | asn; gln |
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in tissue factor protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

A major class of substitutional or deletional variants are those involving the transmembrane, i.e. hydrophobic or lipophilic, region of tissue factor protein. The transmembrane region of tissue factor protein is located at about residues 220 to 242 of the protein encoded by the DNA from human adipose tissues. This region is a highly hydrophobic or lipophilic domain that is the proper size to span the lipid bilayer of the cellular membrane. It is believed to anchor tissue factor protein in the cell membrane.

Deletion or substitution of the transmembrane domains will facilitate recovery and provide a soluble form of recombinant tissue factor protein by reducing its cellular or membrane lipid affinity and improving its water solubility so that detergents will not be required to maintain tissue factor protein in aqueous solution. Preferably, the transmembrane domain is deleted, rather than substituted in order to avoid the introduction of potentially immunogenic epitopes. One advantage of the transmembrane deleted tissue factor protein is that it is more easily secreted into the culture medium. This variant is water soluble and does not have an appreciable affinity for cell membrane lipids, thus considerably simplifying its recovery from recombinant cell culture.

Substitutional or deletional mutagenesis can be employed to eliminate N- or O-linked glycosylation sites (e.g. by deletion or substitution of asparaginyl residues in Asn-X-Thr glycosylation sites), improve expression of tissue factor protein or alter the half life of the protein. Alternatively, unglycosylated tissue factor protein can be produced in recombinant prokaryotic cell culture. Deletions of cysteine or other labile residues also may be desirable, for example in increasing the oxidative stability or selecting the preferred disulfide bond arrangement of the tissue factor protein. Deletions or substitutions of potential proteolysis sites, e.g. Arg Arg, is accomplished for example by deleting one of the basic residues or substituting one by glutaminyl or histidyl residues.

A DNA isolate is understood to mean chemically synthesized DNA, cDNA or genomic DNA with or without the 3' and/or 5' flanking regions. DNA encoding tissue factor protein is obtained from other sources than human by a) obtaining a cDNA library from the placenta, adipose or other tissues containing tissue factor protein mRNA, such as brain, of the particular animal, b) conducting hybridization analysis with labelled DNA encoding human tissue factor protein or fragments thereof (usually, greater than 100 bp) in order to detect clones in the cDNA library containing homologous sequences, and c) analyzing the clones by restriction enzyme analysis and nucleic acid sequencing to identify full-length clones. If full length clones are not present in the library, then appropriate fragments may be recovered from the various clones using nucleic acid sequence disclosed for the first time in the present invention and ligated at restriction sites common to the clones to assemble a full-length clone encoding tissue factor protein.

Tissue factor protein derivatives that are not coagulation-inducing which fall within the scope of this invention include polypeptides that may or may not be substantially homologous with tissue factor protein. These tissue factor protein derivatives are produced by the recombinant or organic synthetic preparation of tissue factor protein fragments or by introducing amino acid sequence variations into intact tissue factor protein so that it no longer demonstrates coagulation-inducing activity as defined above.

Tissue factor protein derivatives that are not coagulation-inducing as described above are useful as immunogens for raising antibodies to coagulation-inducing tissue factor protein. Such tissue factor protein derivatives, referred to as "tissue factor protein antagonists" may be used to neutralize tissue factor protein coagulation-inducing activity. Such a tissue factor protein antagonist may bind to factor VII or VIIa or inhibit the proteolysis of factors IX or X when in complex with factor VII or VIIa. Tissue factor protein antagonists are useful in the therapy of various coagulation disorders e.g. disseminated intravascular coagulation (DIC) occurring during severe infections and septicemias, after surgery or trauma, instead of or in combination with other anticoagulants such as heparin.

Covalent modifications of the tissue factor protein molecule are included within the scope of the invention. Such modifications are made by reacting targeted amino acid residues of the recovered protein with an organic derivatizing agent that is capable of reacting with selected side chains or terminal residues. Alternately, post-translational modification in selected recombinant host cells may be used to modify the protein. The resulting covalent derivatives are useful as immunogens or to identify residues important for biological activity as well as for altering pharmacological characteristics of the molecule, such as half life, binding affinity and the like, as would be known to the ordinarily skilled artisan.

Certain post-translational derivatizations are the result of the action of recombinant host cells on the expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues falls within the scope of this invention.

Other post-translational modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W.H. Freeman & Co., San Francisco pp 79–86 [1983]), acetylation of the N-terminal amine and, in some instances, amidation of the C-terminal carboxyl.

"Essentially free from" or "essentially pure" when used to describe the state of tissue factor protein produced by the invention means free of protein or other materials normally associated with tissue factor protein in its in vivo physiological milieu as for example when tissue factor protein is obtained from blood and/or tissues by extraction and purification. Other materials include infectious organisms such as, for example, the causative agent of acquired deficiency syndrome (AIDS). Tissue factor protein produced by the method of the instant invention is greater than or equal to 95% purity.

In general, prokaryotes are used for cloning of DNA sequences in constructing the vectors useful in the invention. For example, *E. coli* K12 strain 294 (ATCC No. 31446) is particularly useful. Other microbial strains which may be used include *E. coli* B and *E. coli* X1776 (ATCC No. 31537). These examples are illustrative rather than limiting.

Prokaryotes also can be used for expression. The aforementioned strains, as well as *E. coli* W3110 (F⁻, λ⁻, prototrophic, ATTC No. 27325), bacilli such as *Bacillus subtilus*, and other enterobacteriaceae such as *Salmonella typhimurium* or *Serratia marcescans*, and various pseudomonas species can be used.

In general, plasmid vectors containing promoters and control sequences which are derived from species compatible with the host cell are used with these hosts. The vector ordinarily carries a replication site as well as one or more marker sequences which are capable of providing phenotypic selection in transformed cells. For example, *E. coli* is typically transformed using a derivative of pBR322 which is a plasmid derived from an *E. coli* species (Bolivar, et al. Gene 2: 95 [1977]). pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA construction.

Promoters suitable for use with prokaryotic hosts illustratively include the β-lactamase and lactose promoter systems (Chang et al., "Nature", 275: 615 [1978]; and Goeddel et al., "Nature" 281: 544 [1979]), alkaline phosphatase, the tryptophan (trp) promoter system (Goeddel "Nucleic Acids Res."8: 4057 [1980] and EPO Appln. Publ. No. 36,776) and hybrid promoters such as the tac promoter (H. de Boer et al., "Proc. Natl. Acad. Sci. USA" 80: 21–25 [1983]). However, other functional bacterial promoters are suitable. Their nucleotide sequences are generally known, thereby enabling a skilled worker operably to ligate them to DNA encoding tissue factor protein using linkers or adaptors to supply any required restriction sites (Siebenlist et al., "Cell" 20: 269 [1980]). Promoters for use in bacterial systems also will contain a Shine-Dalgarno (S. D.) sequence operably linked to the DNA encoding tissue factor protein.

In addition to prokaryotes, eukaryotic microbes such as yeast cultures may also be used. *Saccharomyces cerevisiae*, or common baker's yeast is the most commonly used eukaryotic microorganism, although a number of other strains are commonly available. For expression in *Saccharomyces*, the plasmid YRp7, for example, (Stinchcomb, et al., Nature 282: 39 [1979]; Kingsman et al, Gene 7: 141 [1979]; Tschemper et al., Gene 10: 157 [1980]) is commonly used. This plasmid already contains the trp1 gene which provides a selection marker for a mutant strain of yeast lacking the ability to grow in tryptophan, for example ATCC no. 44076 or PEP4-1 (Jones, Genetics 85: 12 [1977]). The presence of the trp1 lesion as a characteristic of the yeast host cell genome then provides an effective means of selection by growth in the absence of tryptophan.

Suitable promoting sequences for use with yeast hosts include the promoters for 3-phosphoglycerate kinase (Hitzeman et al., "J. Biol. Chem." 255: 2073 [1980]) or other glycolytic enzymes (Hess et al., "J. Adv. Enzyme Reg." 7: 149 [1968]; and Holland, "Biochemistry" 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., European Patent Publication No. 73,657A. Yeast enhancers also are advantageously used with yeast promoters.

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication. Fiers et al., Nature, 273: 113 (1978). The immediate early promoter of the human cytomegalovirus is conveniently obtained as a HindIII E restriction fragment. Greenaway, P. J. et al., Gene 18: 355–360 (1982). Of course, promoters from the host cell or related species also are useful herein.

Transcription of a DNA encoding tissue factor protein by higher eukaryotes is increased by inserting an enhancer sequence into the vector. Enhancers are cis-acting elements of DNA, usually from about 10 to 300 bp, that act on a promoter to increase its transcription initiation capability. Enhancers are relatively orientation and position independent having been found 5' (Laimins, L. et al., Proc. Natl. Acad. Sci. 78: 993 [1981]) and 3' (Lusky, M. L., et al., Mol. Cell Bio. 3: 1108 [1983]) to the transcription unit, within an intron (Banerji, J. L. et al., Cell 33: 729 [1983]) as well as within the coding sequence itself (Osborne, T. F., et al., Mol. Cell Bio. 4: 1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites.

Expression vectors may contain a selection gene, also termed a selectable marker. Examples of suitable selectable markers for mammalian cells are dihydrofolate reductase (DHFR), thymidine kinase or neomycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR⁻ cells and mouse LTK⁻ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., J. Molec. Appl. Genet. 1: 327 (1982), mycophenolic acid, Mulligan, R. C. and Berg, P. Science 209: 1422 (1980) or hygromycin, Sugden, B. et al., Mol. Cell. Biol. 5: 410–413 (1985). The three examples given above employ bacterial genes under eukaryotic control to convey resistance to the appropriate drug G418 or neomycin (geneticin), xgpt (mycophenolic acid) or hygromycin, respectively.

"Amplification" refers to the increase or replication of an isolated region within a cell's chromosomal DNA. Amplification is achieved using a selection agent e.g. methotrexate (MTX) which inactivates DHFR. Amplification or the making of successive copies of the DHFR gene results in greater amounts of DHFR being produced in the face of greater amounts of MTX. Amplification pressure is applied notwithstanding the presence of endogenous DHFR, by adding ever greater amounts of MTX to the media. Amplification of a desired gene can be achieved by cotransfecting a mammalian host cell with a plasmid having a DNA encoding a desired protein and the DHFR or amplification gene permitting cointegration. One ensures that the cell requires more DHFR, which requirement is met by replication of the selection gene, by selecting only for cells that can grow in the presence of ever-greater MTX concentration. So long as the gene encoding a desired heterologous protein has cointegrated with the selection gene replication of this gene gives rise to replication of the gene encoding the desired protein. The result is that increased copies of the gene, i.e. an amplified gene, encoding the desired heterologous protein express more of the desired heterologous protein.

Preferred suitable host cells for expressing the vectors of this invention encoding tissue factor protein in higher eukaryotes include: monkey kidney CV1 line transformed by SV40 (COS-7, ATCC CRL 1651); human embryonic kidney line (293, Graham. F. L. et al. J. Gen Virol. 36: 59 [1977]); baby hamster kidney cells (BHK, ATCC CCL 10); chinese hamster ovary-cells-DHFR(CHO, Urlaub and Chasin, Proc. Natl. Acad. Sci. (USA) 77: 4216, [1980]); mouse sertoli cells (TM4, Mather, J. P., Biol. Reprod. 23: 243–251 [1980]); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather, J. P. et al., Annals N.Y. Acad. Sci. 383: 44–68 [1982]).

"Transformation" means introducing DNA into an organism so that the DNA is replicable, either as an extrachromosomal element or by chromosomal integration. Unless indicated otherwise, the method used herein for transformation of the host cells is the method of Graham, F. and van der Eb, A., Virology 52: 456–457 (1973). However, other methods for introducing DNA into cells such as by nuclear injection or by protoplast fusion may also be used. If prokaryotic cells or cells which contain substantial cell wall constructions are used, the preferred method of transfection is calcium treatment using calcium chloride as described by Cohen, F. N. et al., Proc. Natl. Acad. Sci. (USA), 69: 2110 (1972).

Construction of suitable vectors containing the desired coding and control sequences employ standard ligation techniques. Isolated plasmids or DNA fragments are cleaved, tailored, and religated in the form desired to form the plasmids required.

For analysis to confirm correct sequences in plasmids constructed, the ligation mixtures are used to transform *E. coli* K12 strain 294 (ATCC 31446) and successful transformants selected by ampicillin or tetracycline resistance where appropriate. Plasmids from the transformants are prepared, analyzed by restriction and/or sequenced by the method of Messing et al., Nucleic Acids Res. 9: 309 (1981) or by the method of Maxam et al., Methods in Enzymology 65: 499 (1980).

Host cells can be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan.

"Transfection" refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but say vary in accordance with the supplier's instructions. After digestion the reaction is electrophoresed directly on a polyacrylamide gel to isolate the desired fragment.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally (Lawn, R. et al., Nucleic Acids Res. 9: 6103–6114 [1981], and Goeddel, D. et al., Nucleic Acids Res. 8: 4057 [1980]).

"Dephosphorylation" refers to the removal of the terminal 5' phosphates by treatment with bacterial alkaline phosphatase (BAP). This procedure prevents the two restriction cleaved ends of a DNA fragment from "circularizing" or forming a closed loop that would impede insertion of another DNA fragment at the restriction site. Procedures and reagents for dephosphorylation are conventional (Maniatis, T. et al., *Molecular Cloning,* 133–134 Cold Spring Harbor, [1982]). Reactions using BAP are carried out in 50 mM Tris at 68° C. to suppress the activity of any exonucleases which may be present in the enzyme preparations. Reactions were run for 1 hour. Following the reaction the DNA fragment is gel purified.

"Ligation" refers to the process of forming phosphodiester bonds between two double stranded nucleic acid fragments (Maniatis, T. et al., Id. at 146). Unless otherwise provided, ligation may be accomplished using known buffers and conditions with 10 units of T4 DNA ligase ("ligase") per 0.5 µg of approximately equimolar amounts of the DNA fragments to be ligated.

"Filling" or "blunting" refers to the procedures by which the single stranded end in the cohesive terminus of a restriction enzyme-cleaved nucleic acid is converted to a double strand. This eliminates the cohesive terminus and forms a blunt end. This process is a versatile tool for converting a restriction cut end that may be cohesive with the ends created by only one or a few other restriction enzymes into a terminus compatible with any blunt-cutting restriction endonuclease or other filled cohesive terminus. Typically, blunting is accomplished by incubating 2–15 µg of the target DNA in 10 mM $MgCl_2$ 1 mM dithiothreitol, 50 mM NaCl, 10 mM Tris (pH 7.5) buffer at about 37° C. in the presence of 8 units of the Klenow fragment of DNA polymerase 1 and 250 µM of each of the four deoxynucleoside triphosphates. The incubation generally is terminated after 30 min. phenol and chloroform extraction and ethanol precipitation.

Human tissue factor protein and its recombinant expression product is obtained according to the following protocol:
1. Oligonucleotide probes representing a single codon choice for each amino acid corresponding to the amino terminal portion of tissue factor protein, and the CNBr peptide fragment were chemically synthesized.
2. Two deoxyoligonucleotides complementary to codons for amino acid sequences of tissue factor protein, described below, were synthesized and radiolabelled with $\gamma^{32}$ P-ATP.

a) 5' CTG ACC TGG AAG TCC ACC AAC TTC AAG ACC ATC-

CTG GAG TGG GAG CCC AAG CCT GTG AAC -3'; and b) 5' ATG GGC CAG GAG AAG GGC GAG TTC CGG GAG ATC-

TTC TAC ATC ATT GGC GCT GTG GTC TTT GTG GTG-

ATC ATC CTG GTG ATC -3'.

3. Oligo (dT) primed cDNA libraries were constructed in λgt10.
4. A human placental cDNA library was screened using the chemically synthesized oligonucleotide probes. No positive plaques were obtained using the 60 mer probe (a). Twenty-two (22) positive plaques were obtained using the 81 mer probe (b), half of which were very weakly positive. The eleven (11) best were chosen to rescreen for plaque purification. Five positive plaques were obtained on the second screen. DNA was prepared from each of these.
5. Clones having a total cDNA of approximately 2800 bp of insert DNA were isolated. Sequencing and characterization of the placental clones were undertaken. Since the mRNA size on a Northern blot was approximately 2.35 Kb these clones may have contained unexcised introns. Hence a human adipose library was screened.
6. An oligo (dT) primed human adipose library was screened using a 1400 bp EcoRI fragment from one of the placental clones.
7. Clones having a total cDNA of approximately 2350 bp (including 150 to 200 bp for the polyA tail) and 1800 bp of insert DNA were isolated. Those clones containing 2350 bp and presumed to contain all the tissue factor mRNA were sequenced.
8. The full length cDNA encoding human tissue factor protein is constructed in a plasmid. It should be appreciated that knowledge of the complete DNA sequence in FIG. 2 enables one to prepare extremely long probes having perfect homology with human tissue factor protein cDNA, thereby considerably simplifying and increasing the efficiency of probing cDNA or genomic libraries from other species, and making it possible to dispense with tissue factor protein purification, sequencing, and the preparation of probe pools.
9. The cDNA encoding human tissue factor protein is then constructed into an expression vehicle which is used to transform an appropriate host cell, which is then grown in a culture to produce the desired tissue factor protein.
10. Biologically active tissue factor protein is produced according to the foregoing procedure has 263 amino acids.

The following examples merely illustrate the best mode now contemplated for practicing the invention, but should not be construed to limit the invention. All literature citations herein are expressly incorporated by reference.

EXAMPLE 1 cDNA Cloning

DNA encoding tissue factor protein may be obtained by chemical synthesis when the complete DNA sequence is known, by screening reverse transcripts of mRNA from liver, or by screening genomic libraries from any cell. Since neither the complete amino acid nor DNA sequence of tissue factor protein were known at the time of this invention, the chemical synthesis of the complete DNA sequence encoding tissue factor protein was not possible.

A human placental cDNA library vas prepared as previously described (Ullrich, A. et al., Nature 309:418–425 [1984]). Double-stranded cDNA was prepared from human adipose RNA using reverse transcriptase in known fashion and, after E. coli RNase H treatment DNA polymerase I was used to synthesize the second strand and then ligated to synthetic oligonucleotides containing restriction sites for SalI, SstI, XhoI and an EcoRI overhanging end, as described previously (Gubler, U. and Hoffman, B. J., Gene 25: 263 [1983]). This DNA was inserted into the EcoRI site of λgt10 (Huynh, T. et al., DNA Cloning, Volume I a practical approach [ed. Glover, D.] [1985].

Two oligonucleotide probes representing one possible codon choice for each of the N-terminal sequence (60 bases) and the internal sequence near the C-terminal (81 bases) were designed and synthesized based on the following amino acid sequences presented at an American Heart Association meeting as cited above:

Amino terminal

5' CTG ACC TGG AAG TCC ACC AAC TTC AAG ACC ATC-

Leu Thr Trp Lys Ser Thr Asn Phe Lys Thr Ile-

CTG GAG TGG GAG CCC AAG CCT GTG AAC -3'

Leu Glu Trp Glu Pro Lys Pro Val Asn

Near C-terminal

5' ATG GGC CAG GAG AAG GGC GAG TTC CGG GAG ATC TTC TAC-

Met Gly Gln Glu Lys Gly Glu Phe Arg Glu Ile Phe Tyr-

ATC ATT GGC GCT GTG GTC TTT GTG GTG ATC ATC CTG GTG ATC-3'

Ile Ile Gly Ala Val Val Phe Val Val Ile Ile Leu Val IlecDNA clones of human tissue factor protein were obtained using the DNA probes first to screen a human placental cDNA library. A 1400 bp EcoRI fragment from a placental clone was used to screen a human adipose cDNA library.

About 1 million phage from the oligo(dT) primed human placenta cDNA library in λgt10 were grown on twenty-five (25) 15-cm petri plates from which triplicate nitrocellulose filters were lifted. The filters were hybridized with each of the $^{32}$P-end labelled oligonucleotide probes in 0.75 M NaCl, 75 mM trisodium citrate, 50 mM sodium phosphate (pH 6.8), 5× Denhardt's solution, 20 percent formamide, 10 percent dextran sulfate and 0.2 g/l boiled, sonicated salmon sperm DNA at 42° C. overnight and washed for 2 hrs in 0.30 M NaCl, 30 mM trisodium citrate, 0.1 percent NaDodSO$_4$ at 42° C. Twenty-two (22) hybridizing duplicate positives were observed with filters hybridized with the tissue factor protein near C-terminal probe. The eleven (11) best were chosen for plaque purification. Tissue factor protein amino terminal probe failed to hybridize. Five clones were positive upon plaque purification. DNA was prepared from each of these and then analyzed by digestion with EcoRI. One clone was shorter and appeared to be a partial clone. Four clones which were identical based on an EcoRI digest were the best candidates for full-length cDNA clones. EcoRI fragments from three of the clones, the partial clone and two of the putative full length clones, were subcloned into M13 phage vectors for DNA sequencing by dideoxy chain termination (Messing, J. et al., Nucleic Acids Res. 9:309–321 [1981]).

A 1400 bp EcoRI fragment from a placental cDNA clone was hybridized to a Northern blot to which was bound mRNA. The size of the tissue factor protein mRNA was determined to be about 2.35 kb in the placental samples which tested positively. The placental cDNA clones were approximately 2800 bp in length including the nucleotides corresponding to the polyA tail on the RNA. These clones were approximately 450 bp longer than the observed length of the mRNA on the Northern blot. Stop codons and methionine codons in all three reading frames were observed immediately upstream of the DNA encoding the amino terminus of the protein, suggesting the absence of a signal sequence. The lack of a signal sequence immediately 5' of the sequence representing the NH$_2$ terminus of the mature protein in the placental clones was confirmed by comparison to the adipose clones described below. It was also determined by comparison of the placental and adipose sequences that the placental clones contained an intervening sequence or intron not present in the adipose clone. The presence of the intron in the placental clone suggests a poor splicing mechanism in the placenta making the isolation and cloning of the pretissue factor protein DNA a most difficult task.

Because of the discrepancy in length between the isolated placental clones and the mRNA as determined in Northern blotting tissue factor protein cDNA was also isolated from an adipose library. An adipose cDNA library constructed in λgt10 was chosen because adipose tissue has amounts of tissue factor mRNA comparable to placental tissue. The library was screened using a 1400 bp EcoRI fragment from a placental clone radiolabelled with γ$^{32}$-P-ATP under conditions more stringent than those used to screen the placental library. (The above conditions were modified to use 50% formamide in the hybridization; and the wash in 0.03M NaCl, 3 mM trisodium citrate, 0.1 percent NaDodSO$_4$, at 60° C.) Fourteen double positives of varying intensities were obtained. Twelve were chosen for plaque purification. Upon rescreening for plaque purification, 8 strong double positives were obtained. DNA was prepared from each of these positives. Four of these, which were identical upon digestion with EcoRI, were the best candidates for full length cDNA clones. One of these was chosen for analysis by DNA sequencing and labeled λTF14. The size of these clones was approximately 2350 bp, including the length of the polyA tail. This was the same size as observed on Northern blot as described above. A fifth clone was shorter than the 2350 bp clones described above.

Two of the adipose cDNA clones were shorter than the full length mRNA (approximately 1800 bp) and had EcoRI digestion patterns which were distinctly different from the putative full length clones. Analysis of these clones indicates that they are partial clones in that they include DNA corresponding to a portion of the tissue factor protein mRNA. The eighth clone was only about 850 bp and was not chosen for further analysis.

EXAMPLE 2

DNA Sequence of Tissue Factor Protein cDNA

The nucleotide sequence of tissue factor protein cDNA is shown in FIG. 2. Of the four adipose clones having an identical EcoRI digestion pattern, one was fully sequenced and corresponded to the sequence shown in FIG. 2. Clone λTF14 contains about 2217 bp of insert, which includes approximately 90 nucleotides of the poly(A) tail (which is not shown in FIG. 2). The cDNA sequence contains 99 bp of 5' untranslated sequence. The EcoRI digestion pattern of the putative full length clone comprised three fragments of about 900, 750 and 650 bp. A fifth clone appeared to differ in the EcoRI digestion pattern in the fragment at the 5' end. Two of the adipose clones had an EcoRI digestion pattern indicating they were shorter than the full length clones but yet contained an EcoRI fragment longer than any fragment in the full length clones. This may be due to an EcoRI polymorphism or to the presence of an intron. The longest clone was sequenced to completion. Completeness of the coding sequence was assessed from the presence of a long open reading frame beginning with a start codon, ATG. Following the ATG initiator codon are codons for a hydrophobic leader or signal sequence.

Figure 5:
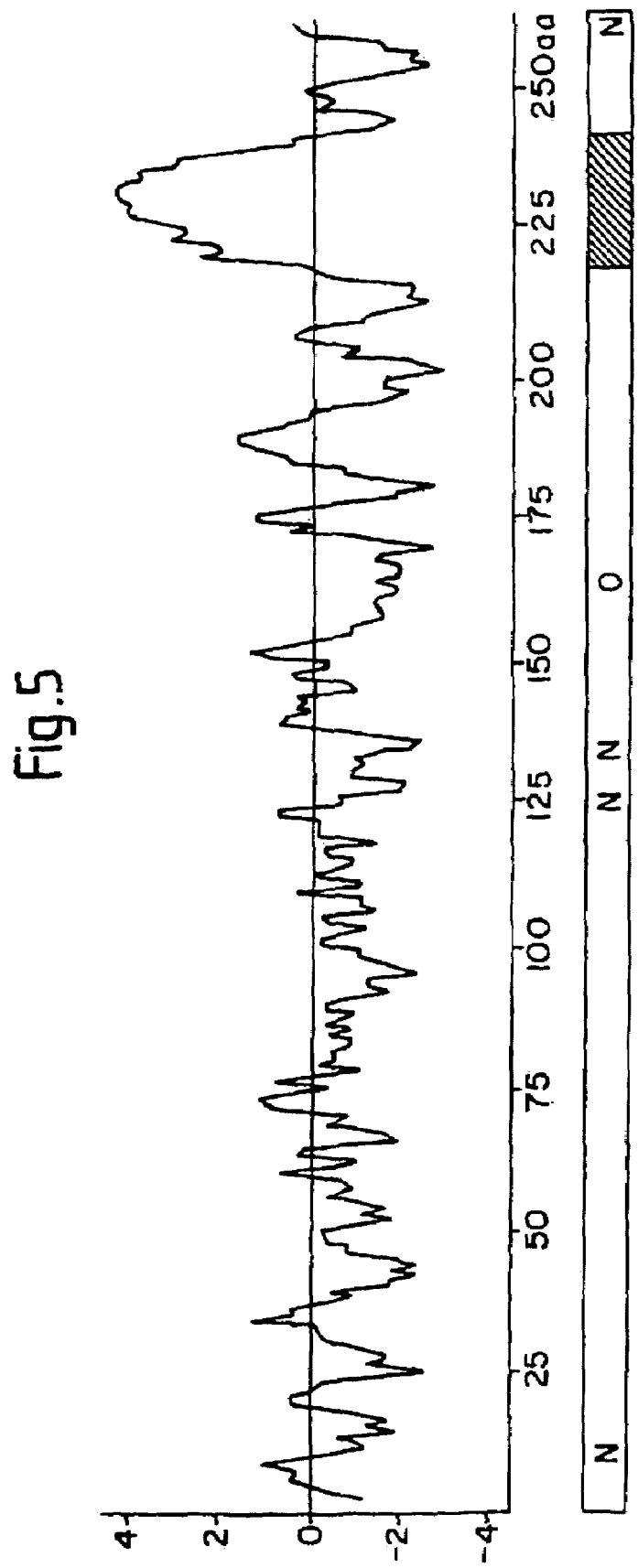
FIG. 5 Hydropathy profile of tissue factor. The translated DNA sequence of human tissue factor vas plotted using the algorithm of Kyte and Doolittle, J. Mol. Biol, 157: 105 (1982). The abscissa shows the amino acid sequence beginning at the mature amino terminus. Positive points in the ordinate denote hydrophobic regions of the protein; each point represents the average hydropathy of 6 successive amino acids. At the bottom, N marks the location of predicted asparagine-linked glycosylation sites and 0 marks the cluster of serine and threonine residues at amino acids 160–172. The predicted hydrophobic membrane spanning domain encompasses residues 220–243 and is indicated by a filled bar.

The 5' end of the cDNA contains an ATG start codon, for the amino acid methionine, followed by a continuous open reading frame that codes for a 295 amino acid polypeptide. The first 32 amino acid residues are mostly hydrophobic amino acids and probably represent an amino-terminal signal peptide. The amino-terminal sequence that follows corresponds to that sequence of tissue factor protein as purified from tissue. The cDNA sequence predicts that the mature tissue factor protein contains 263 amino acids with a calculated molecular weight of about 29,500. Tissue factor protein is known to be a membrane glycoprotein with a relative molecular mass of 42,000 to 53,000 on SDS polyacrylamide gels. The translated DNA sequence predicts four (4) asparagine linked glycosylation sites. A hydropathy profile of the protein (FIG. 5) reveals that the first three of these sites are located in hydrophilic regions, increasing the likelihood that they are on the surface of the protein and indeed glycosylated. Likewise, a cluster of 7 out of 13 residues (amino acids 160–172) that are either serine or threonine, indicating possible sites of O-linked glycosylation, also lies in a predicted region of hydrophilicity. The hydropathy profile also reveals a striking cluster of hydrophobic residues near the carboxy terminus (FIG. 5). This region, encompassing amino acids 220–243, probably comprises the membrane anchoring domain of tissue factor. A search of the sequence data bases revealed no significant homology of tissue factor to available protein sequences. Notably, there was no marked homology to factor VIII, a protein cofactor of the coagulation protease factor IX. This is unexpected because both the factor VIII-factor IX, and the tissue factor—factor VII complexes catalyze the activation of factor X, and the proteases of each complex (factor IX and VII are highly homologous (F. S. Hagen et al., Proc. Natl. Acad. Sci. USA 83:2412 [1986] and S. Yoshitake et al., Biochemistry 24:3736 [1985]). It can now be seen that these interactions are not reflected in a similarity of primary protein sequence of the two cofactors.

The cDNA sequence implies that mature tissue factor is released by signal peptidase cleavage of a prepeptide without additional propeptide processing. The 32 amino acids from the initial methionine to the mature amino terminus commence with a charged region followed by a hydrophobic "core" sequence of 14 residues. The prepeptide ends in ala-gly-ala; ala-X-ala is the most frequent sequence preceding signal peptidase cleavage (O. Perlman et al., Mol. Biol. 167:391 [1983]).

The methionine codon at nucleotide 100–102 (FIG. 2) is presumed to initiate translation of pretissue factor protein. The five nucleotides preceding and the one following this ATG are common choices for nucleotides surrounding translation initiation sites in eukaryotic mRNA, although they are not in complete identity with the concensus described by Kozak, M., Nucl. Acids Res. 12:857 [1984]. The characterized cDNA clones appear to contain virtually the entire 5' untranslated region of the message.

The cDNA contains a 1139 nucleotide 3' untranslated region in which the common polyadenylation signal AATAAA precedes the poly(A) tail by 23 nucleotides. A noteworthy feature of the untranslated region is the presence of a 300 bp Alu family repeat sequence. There are about 300,000 copies of the Alu repeat in the human genome, and numerous examples of their presence in the introns of genes, where they are removed by splicing during the maturation of mRNA (C. W. Schmid et al., Science 216:1065 [1982] and P. A. Sharp, Nature 301:471 [1983]). Although cytoplasmic poly(A)+ RNA also contains Alu sequences, there have only been two previous specific reports of Alu-like sequences in the 3' untranslated sequence of mRNAs: in the class 1 histocompatibility antigens of mouse and rat, and in the human low density lipoprotein receptor (L. Hood et al., Ann. Rev. Immunol. 1:529 [1983]; B. Majello et al., Nature 314:457 [1985] and T. Yamamoto et al., Cell 39:27 [1984]). Alu sequences are often flanked by short direct repeats, as a likely consequence of their insertion into the genome at staggered double-strand nicks. The Alu sequence in the 3' region of tissue factor cDNA is flanked by a direct repeat of 11 nucleotides, as indicated by arrows in FIG. 2.

EXAMPLE 3

Expression of Human Tissue Factor Protein

The full length human tissue factor protein cDNA is contained within the cDNA clone λTF14. The full length cDNA is inserted into an expression plasmid comprising the cytomegalovirus enhancer and promoter, the cytomegalovirus splice donor site and intron, the Ig variable region intron and splice acceptor site, the SV40 polyadenylation and transcription termination site. Construction of the expression vector is undertaken as follows.

The basic vector referred to as pCIS2.8c26D used here has been described in U.S. patent application Ser. No. 06/907,297 which is hereby incorporated by reference. This vector was modified to remove the factor VIII coding sequence by a ClaI-HpaI digest. The region was replaced by a polylinker to allow for additional cloning sites. The sequence of the polylinker used is given below.

```
5' CGATTCTAGACTCGAGGTCCGCGGCCGCGTT 3'

3' TAAGATCTGAGCTCCAGGCGCCGGCGCAA 5'
```

The ClaI and HpaI sites of the original vector are regenerated and sites for enzymes XbaI, XhoI, NotI are added. This vector is called pCIS2.CXXNH. The coding region for tissue factor was subcloned from λTF14 by using the SalI site present at the 5' junction of the λ vector and the cDNA and a NcoI site located 3' of the coding region in the noncoding portion of the cDNA. A blunt 3' end is first created by digesting with NcoI followed by a fill-in reaction containing the Klenow fragment DNA polymerase and 4 dNTP's. When the λTF14 DNA is subsequently cut with SalI an approximately 1232 bp fragment with the sequence TCGA overhanging at the 5' end and a blunt 3' end containing the tissue factor coding region is created. This can be ligated into the pCIS2.CXXNH vector which has been cut with XhoI (yielding a TCGA overhang) and HpaI (blunt). The new vector is labelled pCIS.TF.

Human embryonic kidney cells (293 cells) and monkey kidney cells (Cos cells) are transfected with the expression vector pCIS.TF containing the tissue factor protein cDNA. 48 hours after transfection the cells are harvested and tested for tissue factor protein activity by the chromogenic described below. Tissue factor protein is purified from the cells using techniques previously described for tissue factor protein derived from various tissues (e.g. Bom, J. J. et al., Thrombosis Research 42:635–643 [1986]).

EXAMPLE 4

Assay for Tissue Factor Protein

1. Chromogenic Tissue Factor Assay.

All samples extracted from the cells are relipidated prior to assay. As discussed above tissue factor has an absolute requirement for phospholipid to exhibit activity in in vitro assay systems (Pitlick and Nemerson, Supra). Lecithin granules are homogenized in Tris 0.05 M, 0.1 M NaCl pH7.4 (TBS) containing 0.25% sodium deoxycholate to a concentration of 1 mg/ml. This solution (PC/DOC) is used to relipidate tissue factor as follows. Tissue factor protein is diluted into TBS containing 0.1% bovine serum albumin (TBSA). Fifty microliters are placed in a 12×75 mm polystyrene test tube and 50 µl PC/DOC solution is added. Three hundred and fifty (350) microliters TBSA are then added along with 25 µl 100 mM $CdCl_2$. This relipidation mixture is allowed to incubate at 37° C. for 30 min.

For the chromogenic assay, relipidated tissue factor protein samples are diluted in TBSA. Ten microliters are placed in a test tube with 50 µl of the factor $IX_a$/factor X reagent and 2 µl of a solution of purified factor VII, 30 units/ml. The tubes are warmed to 37° C. and 100 µl 25 mM $CaCl_2$ are added. Samples are incubated for 5 min. at 37° C. prior to the addition of 50 µl chromogenic substrate S2222 containing the synthetic thrombin inhibitor I2581. The reaction is allowed to proceed for 10 min. and is stopped by the addition of 100 µl 50% glacial acetic acid solution. Absorbance is detected at 405 nM. A standard curve is constructed using rabbit brain thromboplastin (commercially available from Sigma, St. Louis, Mo. catalogue #T0263) arbitrarily assigning this reagent as having 100 tissue factor units/ml. Dilutions are made from 1:10 to 1:1000. Absorbance is plotted on the abscissa on semilog graph paper with dilution of standard plotted on the ordinate.

2. One Stage Assay for Tissue Factor Activity.

100 µl haemophilic plasma are added to 10 µl of relipidated or lipid free tissue factor protein or TBSA as control in a siliconized glass tube to prevent non-specific activation through the contact phase of coagulation. The reactants are warmed to 37° C. and 100 µl 25 mM $CaCl_2$ are added and clot formation timed (Hvatum, Y. and Prydz, H., Thromb. Diath. Haemorrh. 21, 217–222 [1969]).

EXAMPLE 5

In Vivo Test of Tissue Factor Protein

The tissue factor protein obtained by the method of the instant invention is assayed for its coagulation inducing capacity in hemophilic dogs by measuring cuticle bleeding time (CBT) (Giles, A. R. et al., supra).

The general methodology is as follows. All animals are lightly anesthetized with a rapid-acting intravenous barbiturate (Bio-Tal [MTC Pharmaceutical, Mississauga, Canada] 5%–18 mg/kg body weight). A continuous infusion is established via a 21-gauge butterfly needle (Abbot-Ireland Ltd., Sligo, Ireland) in the cephalic vein using isotonic saline for injection to keep the vein open. All medications are given via this route.

Prior to injuring the cuticle, all hair is carefully removed by clipping the vicinity of the claw. Silicone grease (Dow Corning, Midland, Mich.) is applied to the claw in order to prevent blood from tracking back beneath the nail. Where the apex of the cuticle can be visualized, it is severed and blood allowed to fall freely by positioning the paw over the edge of the operating table. A spring-loaded sliding blade guillotine nail clipper (Resco, Detroit, Mich.) is used. Where necessary, bleeding is arrested either with silver nitrate applicators (75%, Ingram and Bell, Ltd., Don Mills, Ontario) or the application of topical thrombin (Parke Davis, Detroit, Mich.).

Blood for coagulation assays is anticoagulated with sodium citrate (3.8% w/v), 9 volumes of blood to 1 volume anticoagulant. The prothrombin time (PT) is measured on a Coag-A-Mate 2001 using General Diagnostic reagents (General Diagnostics, Division Warner Lambert Co., Morris Plains, J. J.). The partial thromboplastin time (APTT) is measured manually using cephalin (rabbit brain, Sigma, St. Louis, Mo.) and kaolin (acid washed, Fisher Scientific Co., Fair Lawn, J. J.) as an activator. The thrombin clotting time (TCT) is measured by a modification of the method of Fletcher and coworkers on a fibrometer (B.B.L. Division Becton Dickinson Co., Cockeysville, Md.) following the addition of 0.5 NIH U thrombin (Parke Davis, Detroit, Mich.).

CBTs are performed at specific time intervals and blood samples obtained at similar times. Dogs' cuticles are cut, as described above, and CBT determined. Adequate time passes before dogs are infused with tissue factor protein (50 u/kg) and then cut. CBT is determined.

Pharmaceutical Compositions

The compounds of the present invention can be formulated according to known methods to prepare pharmaceutically useful compositions, whereby the tissue factor protein product hereof is combined in admixture with a pharmaceutically acceptable carrier vehicle. Suitable vehicles and their formulation, inclusive of other human proteins, e.g. human serum albumin, are described for example in Remington's *Pharmaceutical Sciences* by E. W. Martin, which is hereby incorporated by reference. Such compositions will contain an effective amount of the protein hereof together with a suitable amount of vehicle in order to prepare pharmaceutically acceptable compositions suitable for effective administration to the host. Such compositions should be stable for appropriate periods of time, must be acceptable for administration to humans, and must be readily manufacturable. An example of such a composition would be a solution designed for parenteral administration. Although pharmaceutical solution formulations are provided in liquid form appropriate for immediate use, such parenteral formulations may also be provided in frozen or in lyophilized form. In the former case, the composition must be thawed prior to use. The latter form is often used to enhance the stability of the medicinal agent contained in the composition under a wide variety of storage conditions. Such lyophilized preparations are reconstituted prior to use by the addition of suitable pharmaceutically acceptable diluent(s), such as sterile water or sterile physiological saline solution. The tissue factor protein of this invention is administered to provide a coagulation inducing therapeutic composition for various chronic bleeding disorders, characterized by a tendency toward hemorrhage, both inherited and acquired. Examples of such chronic bleeding disorders are deficiencies of factors VIII, IX, or XI. Examples of acquired disorders include: acquired inhibitors to blood coagulation factors e.g. factor VIII, von Willebrand factor, factors IX, V, XI, XII and XIII; haemostatic disorder as a consequence of liver disease which includes decreased synthesis of coagulation factors and DIC; bleeding tendency associated with acute and chronic renal disease which includes coagulation factor deficiencies and DIC; haemostasis after trauma or surgery; patients with disseminated malignancy which manifests in DIC with increases in factors VIII, von Willebrand factor and fibrinogen; and haemostasis during cardiopulmonary surgery and massive blood transfusion.

The invention claimed is:

1. A DNA isolate comprising a DNA sequence encoding a polypeptide having the amino acid sequence shown in FIG. 2.

2. The DNA molecule of claim 1 wherein the nucleotide sequence is

```
ATG GAG ACC CCT GCC TGG CCC CGG GTC CCG CGC CCC GAG ACC GCC

GTC GCT CGG ACG CTC CTG CTC GGC TGG GTC TTC GCC CAG GTG GCC GGC

GCT TCA GGC ACT ACA AAT ACT GTG GCA GCA TAT AAT TTA ACT TGG AAA

TCA ACT AAT TTC AAG ACA ATT TTG GAG TGG GAA CCC AAA CCC GTC AAT

CAA GTC TAC ACT GTT CAA ATA AGC ACT AAG TCA GGA GAT TGG AAA

AGC AAA TGC TTT TAC ACA ACA GAC ACA GAG TGT GAC CTC ACC GAC

GAG ATT GTG AAG GAT GTG AAG CAG ACG TAC TTG GCA CGG GTC TTC TCC

TAC CCG GCA GGG AAT GTG GAG AGC ACC GGT TCT GCT GGG GAG CCT

CTG TAT GAG AAC TCC CCA GAG TTC ACA CCT TAC CTG GAG ACA AAC CTC
```

-continued

```
GGA CAG CCA ACA ATT CAG AGT TTT GAA CAG GTG GGA ACA AAA GTG

AAT GTG ACC GTA GAA GAT GAA CGG ACT TTA GTC AGA AGG AAC AAC

ACT TTC CTA AGC CTC CGG GAT GTT TTT GGC AAG GAC TTA ATT TAT ACA

CTT TAT TAT TGG AAA TCT TCA AGT TCA GGA AAG AAA ACA GCC AAA ACA

AAC ACT AAT GAG TTT TTG ATT GAT GTG GAT AAA GGA GAA AAC TAC TGT

TTC AGT GTT CAA GCA GTG ATT CCC TCC CGA ACA GTT AAC CGG AAG AGT

ACA GAC AGC CCG GTA GAG TGT ATG GGC CAG GAG AAA GGG GAA TTC

AGA GAA ATA TTC TAC ATC ATT GGA GCT GTG GTA TTT GTG GTC ATC ATC

CTT GTC ATC ATC CTG GCT ATA TCT CTA CAC AAG TGT AGA AAG GCA GGA

GTG GGG CAG AGC TGG AAG GAG AAC TCC CCA CTG AAT GTT TCA.
```

3. A recombinant expression vector comprising the DNA molecule of claim 1.

4. A recombinant expression vector comprising DNA encoding human tissue factor protein having the amino acid sequence shown in FIG. 2.

5. A cell transformed with the recombinant expression vector of claim 4.

6. The cell of claim 5 which is a mammalian cell.

7. The cell of claim 5 which is a bacterial cell.

8. A DNA isolate encoding a polypeptide comprising the amino acid sequence of mature tissue factor protein as shown in FIG. 2 from amino acid one to amino acid 263.

9. The DNA molecule of claim 8 wherein the nucleotide sequence is:

```
TCA GGC ACT ACA AAT ACT GTG GCA GCA TAT AAT TTA ACT TGG AAA TCA

ACT AAT TTC AAG ACA ATT TTG GAG TGG GAA CCC AAA CCC GTC AAT CAA

GTC TAC ACT GTT CAA ATA AGC ACT AAG TCA GGA GAT TGG AAA AGC

AAA TGC TTT TAC ACA ACA GAC ACA GAG TGT GAC CTC ACC GAC GAG ATT

GTG AAG GAT GTG AAG CAG ACG TAC TTG GCA CGG GTC TTC TCC TAC COG

GCA GGG AAT GTG GAG AGC ACC GGT TCT GCT GGG GAG CCT CTG TAT

GAG AAC TCC CCA GAG TTC ACA CCT TAC CTG GAG ACA AAC CTC GGA

CAG CCA ACA ATT CAG AGT TTT GAA CAG GTG GGA ACA AAA GTG AAT

GTG ACC GTA GAA GAT GAA CGG ACT TTA GTC AGA AGG AAC AAC ACT

TTC CTA AGC CTC CGG GAT GTT TTT GGC AAG GAC TTA ATT TAT ACA CTT

TAT TAT TGG AAA TCT TCA AGT TCA GGA AAG AAA ACA GCC AAA ACA

AAC ACT AAT GAG TTT TTG ATT GAT GTG GAT AAA GGA GAA AAC TAC TGT

TTC AGT GTT CAA GCA GTG ATT CCC TCC CGA ACA GTT AAC CGG AAG AGT

ACA GAC AGC CCG GTA GAG TGT ATG GGC CAG GAG AAA GGG GAA TTC

AGA GAA ATA TTC TAC ATC ATT GGA GCT GTG GTA TTT GTG GTC ATC ATC

CTT GTC ATC ATC CTG GCT ATA TCT CTA CAC AAG TGT AGA AAG GCA GGA

GTG GGG CAG AGC TGG AAG GAG AAC TCC CCA CTG AAT GTT TCA.
```

10. A recombinant expression vector comprising the DNA molecule of claim 8.

11. The DNA isolate of claim 8 further comprising a nucleic acid sequence encoding a heterologous secretory leader sequence.

12. A recombinant expression vector comprising the DNA molecule of claim 11.

13. A DNA isolate comprising a DNA sequence encoding an amino acid sequence comprising a fragment of the amino acid sequence shown in FIG. 2 capable of inducing coagulation in a coagulation assay.

14. The DNA isolate of claim 13 further comprising a nucleic acid sequence encoding a heterologous secretory leader sequence.

15. The DNA isolate of claim 13 wherein the tissue factor protein further comprises a signal peptide wherein the nucleotide sequence is

```
ATG GAG ACC CCT GCC TGG CCC CGG GTC CCG CGC CCC GAG ACC GCC
GTC GCT CGG ACG CTC CTG CTC GGC TGG GTC TTC GCC CAG GTG GCC GGC
GCT TCA GGC ACT ACA AAT ACT GTG GCA GCA TAT AAT TTA ACT TGG AAA
TCA ACT AAT TTC AAG ACA ATT TTG GAG TGG GAA CCC AAA CCC GTC AAT
CAA GTC TAC ACT GTT CAA ATA AGC ACT AAG TCA GGA GAT TGG AAA
AGC AAA TGC TTT TAC ACA ACA GAC ACA GAG TGT GAC CTC ACC GAC
GAG ATT GTG AAG GAT GTG AAG CAG ACG TAC TTG GCA GCC GTC TTC TCC
TAC CCG GCA GGG AAT GTG GAG AGC ACC GGT TCT GCT GGG GAG CCT
CTG TAT GAG AAC TCC CCA GAG TTC ACA CCT TAC CTG GAG ACA AAC CTC
GGA CAG CCA ACA ATT CAG AGT TTT GAA CAG GTG GGA ACA AAA GTG
AAT GTG ACC GTA GAA GAT GAA CGG ACT TTA GTC AGA AGG AAC AAC
ACT TTC CTA AGC CTC CGG GAT GTT TTT GGC AAG GAC TTA ATT TAT ACA
CTT TAT TAT TGG AAA TCT TCA AGT TCA GGA AAG AAA ACA GCC AAA ACA
AAC ACT AAT GAG TTT TTG ATT GAT GTG GAT AAA GGA GAA AAC TAC TGT
TTC AGT GTT CAA GCA GTG ATT CCC TCC CGA ACA GTT AAC CGG AAG AGT
ACA GAC AGC COG GTA GAG TGT ATG GGC CAG GAG AAA GGG GAA TTC
AGA GAA.
```

16. A recombinant expression vector comprising the DNA molecule of claim 13.

17. A cell transformed with the recombinant expression vector of claim 16.

18. The cell of claim 17 which is a mammalian cell.

19. An isolated DNA molecule encoding a soluble tissue factor protein consisting of the amino acid sequence shown in FIG. 2 up to amino acid residue 242.

20. The DNA molecule of claim 19 wherein one or more of the codons encoding the cysteine residues are substituted with codons encoding other amino acids.

21. The DNA molecule of claim 19 wherein the codons encoding potential Arg Arg proteolysis sites are altered to encode glutamine or histidine or are deleted.

22. The DNA molecule of claim 19 encoding the tissue factor protein having the sequence shown in FIG. 2 between amino acid residues one and 219 and between amino acid residues 243 to 263.

* * * * *

UNITED STATES PATENT AND TRADEMARK OFFICE
CERTIFICATE OF CORRECTION

| | | |
|---|---|---|
| PATENT NO. | : 7,049,131 B1 | Page 1 of 1 |
| APPLICATION NO. | : 08/437989 | |
| DATED | : May 23, 2006 | |
| INVENTOR(S) | : Richard M. Lawn, Gordon A. Vehar and Karen L. Wion | |

It is certified that error appears in the above-identified patent and that said Letters Patent is hereby corrected as shown below:

In the Specification

At column 1, line 4, please add the following paragraph:

--This invention was made with government support under Grant Nos. HL029019 and HL054469 awarded by the National Institutes of Health. The government has certain rights in the invention.--

Signed and Sealed this
Thirtieth Day of September, 2014

Michelle K. Lee
*Deputy Director of the United States Patent and Trademark Office*